Figure 1:
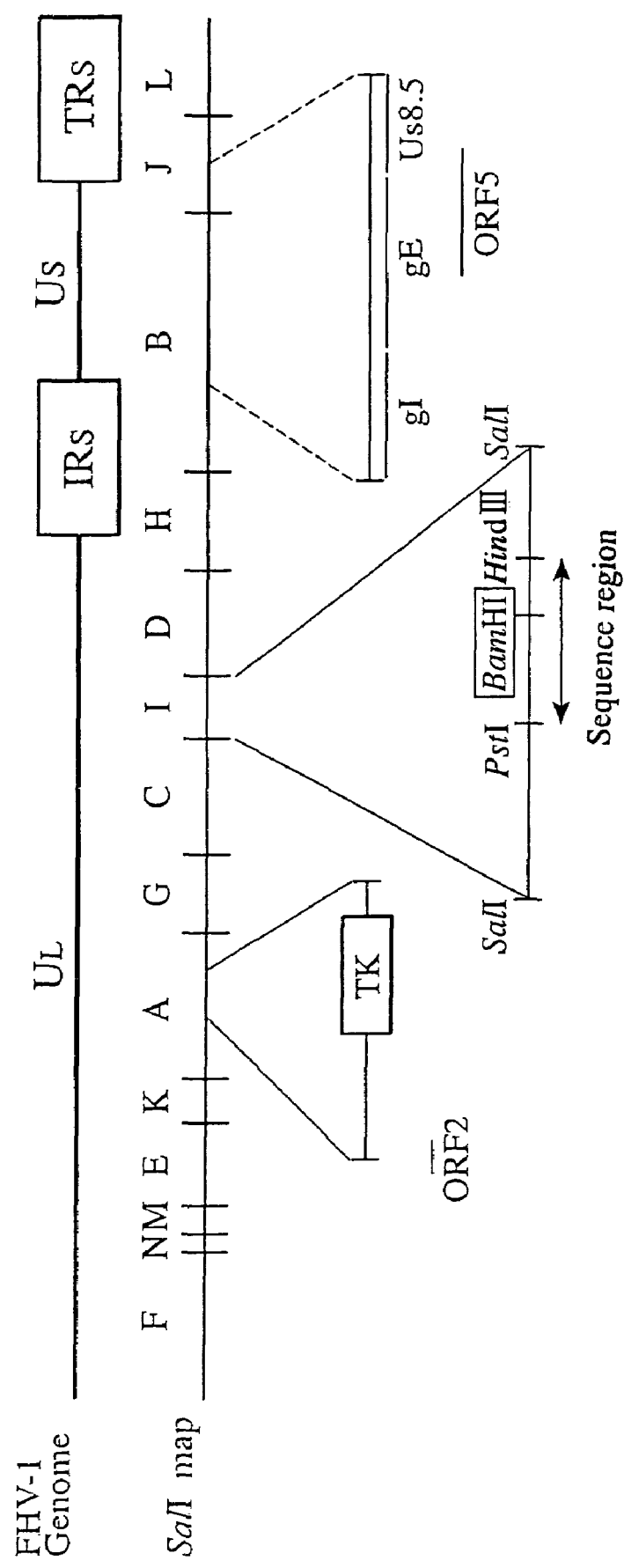

US007297533B2

(12) United States Patent
Kawakami et al.

(10) Patent No.: US 7,297,533 B2
(45) Date of Patent: Nov. 20, 2007

(54) RECOMBINANT FELINE HERPESVIRUS TYPE 1 AND POLYVALENT VACCINE USING THE SAME

(75) Inventors: Kazuo Kawakami, Ibaraki (JP); Masahiko Kishi, Tokyo (JP); Masami Mochizuki, Yokohama (JP)

(73) Assignee: Kyoritsu Seiyaku Corporation (JP)

(*) Notice: Subject to any disclaimer, the term of this patent is extended or adjusted under 35 U.S.C. 154(b) by 594 days.

(21) Appl. No.: 10/398,696

(22) PCT Filed: Oct. 5, 2001

(86) PCT No.: PCT/JP01/08830

§ 371 (c)(1),
(2), (4) Date: Apr. 4, 2003

(87) PCT Pub. No.: WO02/29063

PCT Pub. Date: Apr. 11, 2002

(65) Prior Publication Data

US 2005/0089531 A1 Apr. 28, 2005

(30) Foreign Application Priority Data

Oct. 5, 2000 (JP) ............................ 2000-306802

(51) Int. Cl.
*C12N 15/63* (2006.01)
*A61K 48/00* (2006.01)
(52) U.S. Cl. ............... 435/320.1; 435/91.4; 435/91.41; 435/91.42; 424/229.1
(58) Field of Classification Search ............. 435/320.1, 435/91.4, 91.41, 91.42; 424/229.1, 199.1
See application file for complete search history.

(56) References Cited

U.S. PATENT DOCUMENTS 6,074,649 A 6/2000 Audonnet et al.

FOREIGN PATENT DOCUMENTS

| | | |
|---|---|---|
| EP | 0576092 A1 | 12/1993 |
| JP | 09-000267 | 7/1997 |
| WO | WO 90/01547 | 2/1990 |
| WO | WO 94/03621 | 2/1994 |
| WO | WO 95/00172 A1 * | 1/1995 |
| WO | WO 97/20059 | 6/1997 |
| WO | WO 98/50069 | 11/1998 |

OTHER PUBLICATIONS animalclinic.com/FELVEASY.htm.*

Eiji Sato et al. "Efficient expression of the envelope protein of feline immunodeficiency virus in a recombinant feline herpesvirus type 1 (FHV-1) using the gC promoter of FHV-1", Virus Research, Sep. 2000, p. 13-23, vol. 70, Nos. 1-2.

N. Yokoyama et al., "Pathogenicity and vaccine efficacy of a thymidine kinase-deficient mutant of feline herpesvirus type 1 in cats", Archives of Virology, 1996, p. 481-494, vol. 141.

N. Yokoyama et al., "Vaccine efficacy of recombinant feline herpesvirus type 1 expressing immunogenic proteins of feline calicivirus in cats", Archives of Virology, 1996, p. 2339-2351, vol. 141.

Jack H. Nunberg et al., "Identification of the Thymidine Kinase Gene of Feline Herpesvirus: Use of Degenerate Oligonucleotides in the Polymerase Chain Reaction To Isolate Herpesvirus Gene Homologs", Journal of Virology, Aug. 1989, p. 3240-3249, vol. 63, No. 8.

Naoaki Yokoyama et al., "Construction of the Recombinant Feline Herpesvirus Type 1 Deleted Thymidine Kinase Gene", J. Vet. Med. Sci., 1995, p. 709-714, vol. 57, No. 4.

Georgette E. Cole et al., "Recombinant Feline Herpesviruses Expressing Feline Leukemia Virus Envelope and *gag* Proteins", Journal of Virology, Oct. 1990, p. 4930-4938, vol. 64, No. 10.

Richard C. Wardley et al., "The use of feline herpesvirus and baculovirus as vaccine vectors for the *gag* and *env* genes of feline leukaemia virus", Journal of General Virology, 1992, p. 1811-1818, vol. 73, Printed in Great Britain.

Marja J. Willemse et al., "The gene downstream of the gC homologue in feline herpes virus type 1 is involved in the expression of virulence", Journal of General Virology, 1994, p. 3107-3116, vol. 75, Printed in Great Britain.

Marja J. Willemse et al., "In vivo properties of a feline herpesvirus type 1 mutant carrying a lacZ insertion at the gI locus of the unique short segment", Vaccine, 1996, p. 1-5, vol. 14, No. 1, Elsevier Science Ltd., Printed in Great Britain.

Michael D. Sussman et al., "A Feline Herpesvirus-1 Recombinant with a Deletion in the Genes for Glycoproteins gI and gE Is Effective as a Vaccine for Feline Rhinotracheitis", Virology 1995, p. 12-20, vol. 214.

Randall F. Smith et al., "Identification of New Protein Kinase-Related Genes in Three Herpesviruses, Herpes Simplex Virus, Varicella-Zoster Virus, and Epstein-Barr Virus", Journal of Virology, Jan. 1989, p. 450-455, vol. 63, No. 1, American Society of Microbiology.

M. S. Chee et al., "Alpha-, Beta- and Gammaherpesviruses Encode a Putative Phosphotransferase", J. gen. Virol., 1989, p. 1151-1160, vol. 70, Printed in Great Britain.

(Continued)

*Primary Examiner*—Bruce Campell
*Assistant Examiner*—Baon Qun Li
(74) *Attorney, Agent, or Firm*—Kilpatrick Stockton LLP

(57) ABSTRACT

An attenuated feline recombinant herpesvirus 1 (FHV-1), which is prepared by identifying gene regions in the genome wherein inserted foreign genes can be expressed without affecting the replication of FHV-1 and has least two types of foreign nucleic acid sequences inserted thereinto, usable as a vector virus or a vaccine. In this attenuated recombinant FHV-1, at least two types of foreign genes are inserted in such a manner as allowing the expression into two different gene regions exerting no lethal effect on the proliferation of the virus in the feline herpesvirus 1 genome.

9 Claims, 12 Drawing Sheets

OTHER PUBLICATIONS

Guy Bradley et al., "Structure of the Marek's Disease Virus *Bam*Hl-H Gene Family: Genes of Putative Importance for Tumor Induction", Journal of Virology, Jun. 1989, p. 2534-2542, vol. 63, No. 6, American Society for Microbiology.

Robert A. Crandell et al., "Development, Characterization, and Viral Susceptibility of a Feline (*Felis catus*) Renal Cell Line (CRFK)", In Vitro, 1973, p. 176-185, vol. 9, No. 3.

Takayuki Miyazawa et al., "Establishment of a feline T-lymphoblastoid cell line highly sensitive for replication of feline immunodeficiency virus", Archives of Virology, 1989, p. 131-135, vol. 108.

Tsutomu Hohdatsu et al., "Comparative study of the cell tropism of feline immunodeficiency virus isolates of subtypes A, B and D classified on the basis of the *env* gene V3-V5 sequence", Journal of General Virology, 1996, p. 93-100, vol. 77, Printed in Great Britain.

Paul A. Rota et al., "Physical Characterization of the Genome of Feline herpesvirus-1", Virology, 1986, p. 168-179, vol. 154.

A. Grail et al., "Restriction endonuclease mapping of the genome of feline herpesvirus type 1", Archives of Virology, 1991, p. 209-220, vol. 116.

Niels de Wind et al., "Herpesviruses Encode an Unusual Protein-Serine/Threonine Kinase Which Is Nonessential for Growth in Cultured Cells", Journal of Virology, Sep. 1992, p. 5200-5209, vol. 66, No. 9, American Society for Microbiology.

Marja J. Willemse et al., "Transcriptional Analysis of the Short Segment of the Feline herpesvirus Type 1 Genome and Insertional Mutagenesis of a Unique Reading Frame", Virology 208, 1995, vol. 208.

Kruger, J M et al., "Glycoproteins GL and gE of Feline Herpesvirus-1 Are Virulence Genes: Safety and Efficacy of a gl-gE-Deletion Mutant in the Natural Host", Virology, Academic Press, Orlando, US, vol. 220, 1996, pp. 299-308.

\* cited by examiner

FIG.2A

FHV-1 Genome — UL — IRs — Us — TRs (SalI frag.) F NM E K A G C I D H B J L

TK

FCV Capsid dTK-gC/Cap-FHV

FIG.2B

FHV-1 Genome — UL — IRs — Us — TRs (SalI frag.) F NM E K A G C I D H B J L

BamHI

LacZ

Lac FHV

FIG.2C

FHV-1 Genome — UL — IRs — Us — TRs (SalI frag.) F NM E K A G C I D H B J L

TK                BamHI

FCV Capsid      LacZ

FHV-Cap/Lac

FIG.4

CMVpro β-galactosidase
SV40 poly A
SalI    SalI
BamHI
pdBSI-LacZ
Transfection

FHV-1

CrFKcells ← Infection

⬇

Homologous genetic recombination

⬇

Lac-FHV dTK-gC/Cap-FHV → Infection    Infection ⬇

CrFKcells

⬇

Homologous genetic recombination

⬇

FHV-Cap/Lac

FIG.11

```
FHV-1 PK AA    1:MARRGGRSATDEMDVGGSSQGDPLSH-GPILSPITRPSSGVREGGHCNTADPHSQGNHI  59
HSV-1 PK AA    1:-----------------------------------------------------------   1
EHV-1 PK AA    1:MARSRRRSSVDEMDVGGSATSEYENCGPSFSPLNLSRPKKSTRG-RSLRSAQAWGGKQL  59
EHV-4 PK AA    1:MARSRGRSSVDEMDVGGSTTSEYENCDGPSFSPLNMSCAKKSTKK-RSLRSSRIWGGKSS  59

FHV-1 PK AA   60:KRGICKPGVSGSGNTADSAHKHLTMSPRRLRPLPHREGILRHRIKEECQDFQ-AGNGEGK 118
HSV-1 PK AA    1:-----------------------MDESRR-QRPAGHVAANLSPQGARQRS-FKDWLASYVH  36
EHV-1 PK AA   60:HPERSTP-LARNDCGPSSKPRRHEVGRSNK-GLGAS--LDRTDEDTS------Q-CPR  107
EHV-4 PK AA   60:DSEHT-PLLTRNSCGPTGNTRRKHAGISNHKRG--AS--LNHENGDKSF----Q-SGHNCPR 111

FHV-1 PK AA  119:IRANTAIDRYFTRARRIFKYTPRRMSSRRGGRTTPPCMAGWASPSGGRYDGLIRGDSNNG 178
HSV-1 PK AA   37:SNPHGASGRPSGPS--LQDAAVSRSS--HGSRHRSGLR-ERLRAGLSRWRMSRSSHRRAS  91
EHV-1 PK AA  108:IRASAI--RCGASTRKIVRITGECDAQQGDSRPGRSEMAGWHSPPKRRRTPSRHGNSDNE 165
EHV-4 PK AA  112:IRASAV--RCGAATRKIVRITEEGASRQDNIWPGQSGMAGWHSPPKRRRTPSRHGDSNHE 169

FHV-1 PK AA  179:RTDIPN--TLTRIPIHEVCTPLTTNPGNRSSILKIRKIKRVTIPVFSVSAEMHYSKVALG 236
HSV-1 PK AA   92:PETPGTAAKLNRPLRRSQAALTAPPSSPSHILTTRIKLCSPVFAINPALHYTTLEIP   151
EHV-1 PK AA  166:RSHLPR--LSSHGVRVGGRPLTQTPLQKTIILQPKLVRKVFMPTFTVNPEMHYRRVALG  223
EHV-4 PK AA  170:RSHLSG--QPSQSVVRVGGRLLTQTPLRKTIILQPKLVRKVFMPTFTVNPGMHYRRVSLG  227

I                          II
FHV-1 PK AA  237:EPPK FGGAGGYGEVQ IYRQTGLAIK TSSSPSCFEHELLVTLLAGESSLRARSSIGITGII  296
HSV-1 PK AA  152:GARS FGGSGGYGDVQ LIREHKLAVK TIKEKEWFAVELIATLLVGECVLRAGRTHNIRGFI  211
EHV-1 PK AA  224:EIPK FGAGSYGEVQ IFKQTGLAIK TASSRSCFEHELAVSLLTGECSLRAQASLGIGGII  283
EHV-4 PK AA  228:ETPK FGAGSYGEVQ IFKQNGLAIK TSSSRSCFEHELAVSLLTGECSLRAQSTLGIGGII  287
                     *****             ****            ****
```

(CONTINUE)

(FIG. 11 CONTINUED)

```
EHV-1 PK AA 297:YPVAFSLTEHQMVFKAYDMDLNVYCNKLSSAGPPTSNILNAMEHAFIGLGKAVAYLNTKC 356
HSV-1 PK AA 212:APLGFSLQQRQIVFPAYDMDLGKYIGQLASLRTINPSVSTALHQCFTELARAVVFLNTTC 271
EHV-1 PK AA 284:CLMAFSLPSKQMVFPAYDADLNAYGYRLSRSGPPSVLVTESIERAFIGLGRALVYLNTSC 343
EHV-4 PK AA 288:CLMAFSLPSKQMVFPAYDADLNAYGYRLSRNGPPSVLVTESIERAFIGLGRALVYLNTSC 347
                                            III                               IV
EHV-1 PK AA 357:QLTHLDIKCGNIFVNTKNCVIKDYV-IA-DFSLMTLNTNSTVMRAEFEIPTGDASNKVLR 414
HSV-1 PK AA 272:QISHLDIKCANILVMLRSDAVSLRRAVLADFSLVTLNSNSTIARGQFCLQEPDLKSPRMF 331
EHV-1 PK AA 344:QLTHLDVKGGNIFVNHSHFVISDCV-IG-DLSLMTLNTNSMAMRAEFEIDTGEEIKTLR 401
EHV-4 PK AA 348:QLTHLDVKGGNIFVNHSHFVISDCV-IG-DLSLMTLNTNSMAMRAEFEIDTGEEIKTLR 405
                 *****                      *             ***
                                     V                              VI
EHV-1 PK AA 415:-LSRGAATT-IFSLVLGHGHNQPTEILVDFINNSGLARIHRGPLDSDVGVADLYALGQVL 472
HSV-1 PK AA 332:GMPT-ALTTANFHILVGHGYNQPPELLVKYLNNERAEFTNHRLKHDVGLADLYALGQTL 390
EHV-1 PK AA 402:-LPRSASQM-TFSFVIGHGLNQPISVIADFINNSGLAKSTGPIKHDVGLTIDLYALGQAL 459
EHV-4 PK AA 406:-LPKSASQM-TFSFVGHGHNQPLSVIADFINNSGLAKNTGPIKHDVGLAVDLYALGQAL 463
                     *             *                                  ******
                 VI
EHV-1 PK AA 473:LELLLTGCLSPRLPVPILRNTTYYYLHQVTVEYALDLLAYLR-TIPPYISFF------T 525
HSV-1 PK AA 391:LELVVSYVYAPSLGVPVTRFPGYQYFNNQLSPDFALALLAY-RCVLHPAL-FVNS-AETN 447
EHV-1 PK AA 460:LELLLVGCISPCLSVPILRTATYYYSNKLSVDYALDLLAY-RCSL---YPALFPTIPLIT 516
EHV-4 PK AA 464:LDLLLVGCISPCLSVPILRTATYYYSNRLSVDYALDLLAY-RCSL---YPAIFPTTPLIT 520
                ****   **  **   *

EHV-1 PK AA 526:YYNNSWCS-----------I----------- 534
HSV-1 PK AA 448:THGLAYIDVPEGIRRHLRNPKIRRAFTDRCINYQHTHKAILSSVALPPELKPLLVLVSRLC 507
EHV-1 PK AA 517:IYGIPWDQVEGVFESIAGAHHREAF--RA----------H---LE 546
EHV-4 PK AA 521:IYGIPWDQVEGVFESIAGAHHREAF--RA----------H---LD 550

EHV-1 PK AA 535:---------PC---- 536
HSV-1 PK AA 508:HTNPCARHALS 518
EHV-1 PK AA 547:------RYRL--- 550
EHV-4 PK AA 551:------RYRL--- 554
```

RECOMBINANT FELINE HERPESVIRUS TYPE 1 AND POLYVALENT VACCINE USING THE SAME

CROSS-REFERENCE TO RELATED APPLICATION

This application claims the benefit of International Application No. PCT/JP01/08830 filed Oct. 5, 2001.

TECHNICAL FIELD

This invention relates to use of feline herpesvirus type 1 (abbreviated hereinafter into FHV-1) as a vector virus.

BACKGROUND ART

With respect to a gene of a virus whose host is a cat, a recombinant virus vector not naturally occurring has been created by artificially deleting, by genetic engineering technology, a part of the genome DNA of FHV-1, which is a herpesvirus belonging to an alphaherpes virinae subfamily of Herpesviridae and inducing viral nasal tracheitis in cats, and then introducing a foreign gene into the deleted region so as to express it in cells or animal bodies. It is known that such a recombinant vector upon infection of cells or animals produces not only a viral antigen derived from FHV-1 but also a product derived from the foreign gene, and upon inoculation into animals, gives immunity to the foreign gene product in addition to FHV-1 (N. Yokoyama et al., 1996, Arch. Virol. 141: 481-494; N. Yokoyama et al., 1996, Arch. Virol. 141: 2339-2351).

As an example of a such FHV-1 vector, a recombinant virus vector constructed by deleting a thymidine kinase (abbreviated hereinafter into TK) gene region and inserting a foreign gene into the deleted site is known (J. H. Nunberg et al., 1989, J. Virol. 63: 3240-3249; N. Yokoyama et al., 1995, J. Vet. Med. Sci. 57: 709-714). Such recombinant FHV-1 is confirmed to express not only FHV-1 protein but also a protein derived from the foreign gene introduced into the TK gene region, without damaging the ability to replicate the virus (G. H. Cole et al., J. Virol. 1990, 64: 4930-4938; R. C. Wardley et al., 1992, J. Gen. Virol. 73: 1811-1818). Further, Yokoyama et al. (N. Yokoyama et al., 1996, Arch. Virol. 141: 2339-2351) have reported that recombinant FHV-1 having a foreign gene inserted into the TK gene region is not pathogenic to cats, and a cat inoculated with the recombinant FHV-1 produces an antibody to a product of the foreign gene.

On one hand, an open reading frame 2 (ORF2) located downstream from the region of gC gene in the unique long ($U_L$) region is known as an insertion site for a foreign gene other than the TK gene region in FHV-1 genome. Willemse et al. (M. J. Willemse et al., 1994, J. Gen. Virol. 75: 3107-3116) have reported that recombinant FHV-1 having a β-galactosidase-encoding gene (abbreviated hereinafter into LacZ) fragment as a foreign gene inserted into ORF2 maintains the same ability to replicate the virus as that of attenuated FHV-1. Further, it is also known that gene regions such as Us 8.5, gI and gE in the unique short (Us) region of the FHV-1 genome are not necessarily required for replication of FHV-1.

With respect to the recombinant FHV-1 having a foreign gene inserted into such a gene region, it is reported that recombinant FHV-1 having LacZ inserted into the $U_S$ 8.5 gene region maintains the same ability to replicate the virus as that of attenuated FHV-1 (M. J. Willemse et al., 1995, Virology 208: 704-711), while it is reported that recombinant FHV-1 having LacZ inserted into gI and gE gene regions has significantly reduced the replication ability as compared with that of attenuated FHV-1 (M. J. Willemse et al., 1996, Vaccine 14: 1-5; M. D. Sussman et al., 1995, Virology 214: 12-20). In addition to recombinant FHV-1 using the Us gene region as an insertion site for a foreign gene, recombinant FHV-1 having a foreign gene inserted into ORF5 (nucleotide positions 5869-7113) of the FHV-1 genome has been proposed (Japanese Patent Application National Publication (Laid-Open) No. 2000-501927). However, the safety of these recombinant virus vectors to animals is not examined, and thus whether or not they are pathogenic to cats as the host is not evident. For reference, these insertion sites for foreign genes, together with a SalI map, are shown in a part of FIG. 1.

With respect to the recombinant FHV-1, several sites in the FHV-1 genome have been identified as insertion sites for foreign genes as described above, but there is no report on construction of a recombinant FHV-1 vector having a plurality of foreign genes inserted simultaneously into a plurality of gene insertion sites.

In consideration of application to a vaccine, a recombinant FHV-1 vector prepared by conventional techniques, including FHV-1 itself, can be used as a divalent vaccine, assuming that one type of foreign gene is inserted into essentially one gene insertion site. However, this does not meet a recently increasing demand for trivalent or more feline vaccines.

For maintaining the life cycle of virus, phosphorylation of viral protein is necessary, and cellular or viral protein kinases (protein phosphatase: serine/threonine kinase and tyrosine kinase) are considered to be involved in this phosphorylation. With respect to herpes simplex virus type 1 (HSV-1) and varicella-zoster virus (VZV) which like FHV-1, belong to the alpha-herpesvirus subfamily and Epstein-Barr virus (EBV) classified into the gamma-herpesvirus subfamily, the presence of a gene sequence encoding protein kinase in their virus genome is known, and an amino acid sequence encoded by the gene is concerved highly among the respective herpesviruses.

It is reported that in particular, catalytic domains I to VI in protein kinase are highly conserved among various herpesviruses (R. F. Smith, and T. F. Smith, 1989, J. Virol. 63: 450-455). A typical amino acid sequence of domain I in the catalytic domains of herpesvirus protein kinase is GXGXXGXV (SEQ ID NO.12)(X is a lowly conserved amino acid), and it has been found that such an amino acid sequence is highly conserved among HSV-1, VZV, EBV, human cytomegalovirus (HCMV) and human herpesvirus type 6 (HHV-6) (M. S. Chee, G. J. Lawrence, and B. G. Barrel. 1989, J. Gen. Virol. 70: 1151-1160).

In the prior art, however, there is no report on construction of a recombinant FHV-1 vector which except for TK gene-defective recombinant FHV-1 vector, is sufficiently attenuated to be safe to a cat, maintains a sufficient ability to replicate the virus produced as a vaccine virus and gives immunity simultaneously to three or more kinds of pathogenic gene products including FHV-1 itself. That is, in the known recombinant FHV-1 vector, the site into which a foreign gene can be inserted is limited essentially to one region in the FHV-1 genome, so that the cat inoculated with the recombinant FHV-1 is expected to have immunity to only one kind of foreign antigen besides FHV-1.

For providing the cat with immunity for protection against infection with, for example, 3 kinds of pathogenic microorganisms including FHV-1, it is therefore necessary to inoculate the cat with the recombinant FHV-1 having one kind of foreign gene inserted into it, and to further inoculate the cat with another kind of intended pathogenic microorganism or a vaccine consisting of an antigen derived therefrom. This, in production of vaccines, causes diversification of products and production processes, significantly increases production costs, and easily increases side effects due to inoculation with a plurality of vaccines consisting of pathogenic microorganisms.

On one hand, homologous genetic recombination between a vector virus and a naturally contagious virus in an animal is problematic upon the inoculation of a vector virus into an intended animal, and there is anxiety that the attenuated vector virus can acquire pathogenicity through the genetic recombination. To reduce such acquisition of pathogenicity by the attenuated vector virus through genetic recombination, it is necessary that gene mutations are induced in plural sites of the vector virus genome or foreign gene fragments are introduced into such sites, followed by homologous genetic recombination between the vector virus genome and the pathogenic virus genome, whereby the conversion of the vector virus into a pathogenic virus can be prevented unless gene sequences in the plural sites of the vector virus genome are simultaneously converted into pathogenic viruses. At present, however, the attenuated recombinant FHV-1 vector wherein a plurality of such gene regions are converted into gene sequences different from those of the pathogenic virus, or foreign genes are simultaneously introduced into a plurality of gene regions has never been created, mainly because the replication ability of the vector virus is lost.

For vaccines used in the prevention of feline viral infections or microbial infections, specifically vaccines for preventing infections with feline calicivirus, feline panleukopoenia virus, feline leukemia virus, rabies virus, FHV-1 and chlamydia, either the attenuated vaccines or inactivated vaccines are administered by a method of inoculation by injection. However, the method of inoculation by injection is not necessarily the best method because of the attendant troublesome procedures, and sharp pain for the animals. On the other hand, the method of inoculation via the mucosa, such as eye-dropping or nasal or oral inoculation, is superior to the method of inoculation by injection in many respects such as an easier inoculation procedure and induction of immunity via the mucosa without causing pain to the animals being inoculated.

DISCLOSURE OF INVENTION

The inventors made study for solving the problems described above and further improved the known TK-defective attenuated recombinant FHV-1 vector (JP-A 9-267). That is, the inventors found that a BamHI cleavage site in an I fragment located in the $U_L$ region out of SalI digested DNA fragments (abbreviated hereinafter into I fragment) of the FHV-1 genome is identified as a new foreign gene insertion site exerting no lethal effect on the replication and proliferation of FHV-1, whereby the recombinant FHV-1 maintains the ability to replicate the virus, while a product of the inserted foreign gene is expressed. Then, the inventors revealed that a gene region encoding protein kinase is present in the vicinity of the BamHI site in this I fragment, whereby this invention was completed.

Further, the inventors constructed a recombinant FHV-1 utilizable as a vector, comprising different foreign genes inserted into the gene regions of both the I fragment and the known TK gene within one viral genome. The inventors found that the virus (virus vector) thus constructed can be replicated in cells infected therewith or in a cat body inoculated therewith via the mucosa, and also that products of at least two types of foreign genes inserted into the recombinant FHV-1 genome are produced in the infected cells or the cat body, and this invention was thereby completed.

That is, the attenuated recombinant feline herpesvirus type 1 of the invention comprises at least two types of foreign genes inserted in such a manner as to allow the expression into two different gene regions in the feline herpesvirus type 1 genome, wherein the two types of different regions in the feline herpesvirus type 1 genome, into which at least two types of foreign genes are inserted in such a manner as to allow the expression, are two regions exerting no lethal effect on the proliferation of the feline herpesvirus type 1. Specifically these regions are two gene regions, that is, an I fragment region of SalI digested DNA fragments, that presents in the unique long ($U_L$) region of the feline herpesvirus type 1 genome, and a gene region encoding thymidine kinase, or two gene regions, that is, a gene region encoding protein kinase present in the unique long ($U_L$) region in the feline herpesvirus type 1 genome and a gene region encoding thymidine kinase.

Protein kinase present in the unique long ($U_L$) region in the feline herpesvirus type 1 genome comprises an amino acid sequence set forth in SEQ ID NO:2, and accordingly, the insertion sites for foreign genes can be not only the coding gene region in the I fragment region, but also the whole of the gene region encoding protein kinase.

The term "in such a manner as to allow the expression" in this invention means that a foreign gene or a gene fragment consisting of a part of the gene is inserted and simultaneously linked with gene expression regulatory sequences such as a promoter and enhancer so as to allow the inserted foreign gene to express its gene product in cells. Sequences such as a promoter etc. which are gene expression regulatory sequences for enabling expression of the foreign gene may, together with the foreign gene, be inserted as a part of the foreign gene to be inserted, or the foreign gene as a structural gene may be inserted and arranged in such a manner as to allow the feline herpesvirus type 1 (FHV-1) itself to utilize gene expression regulatory sequences such as a promoter etc. in the genome. That is, the inserted foreign gene in this invention may be in the form of a structural gene only or a gene cassette having a structural gene combined with gene expression regulatory sequences such as a promoter etc. The gene cassette having a structural gene combined previously with a gene expression regulatory sequence such as a promoter etc. is preferably used to ensure the expression of a gene product of the inserted foreign gene and to secure the degree of freedom of the insertion site.

In the insertion of a foreign gene into the I fragment region, the presence of gene expression regulatory sequences such as a promoter etc. necessary for expression of the foreign gene in the I fragment, particularly in a BamHI recognition site as the insertion site for the foreign gene is not evident. Further, even if the gene expression regulatory sequences are present in the vicinity of the BamHI recognition site, the mechanism of insertion of the foreign gene is homologous genetic recombination occurring between the transfer vector and the FHV-1 genome. For this reason, the foreign gene is not always inserted into a site where the expression of the foreign gene is regulated efficiently by the gene expression regulatory sequences. Accordingly, the foreign gene is inserted preferably as a gene cassette containing gene expression regulatory sequences such as a promoter etc. When the foreign gene is to be inserted into the gene region encoding protein kinase, it is also preferable, for the same reason, that the foreign gene is inserted preferably as a gene cassette containing gene expression regulatory sequences such as a promoter etc.

The gene expression regulatory sequences such as a promoter etc. include the gC promoter and gB promoter derived from FHV-1, an immediate early (IE) promoter from human cytomegalovirus (HCMV), and an RNA 1.8 promoter derived from Marek's disease virus (MDV) (G. Bradley et al., 1989, J. Virol. 63: 2534-2542). Among these, the gC promoter derived from FHV-1 is particularly preferable in respect of production of the foreign gene product at the same level as in natural infection with FHV-1, and the IE promoter from human cytomegalovirus is particularly preferable in respect of active production of the foreign gene product by the high activity of the promoter, to achieve strong immunogenicity by the expressed gene product.

In the case of the insertion of a foreign gene into the gene region encoding thymidine kinase, on the other hand, gene expression regulatory sequences such as a promoter, enhancer etc. for expression of thymidine kinase are present in the vicinity of the insertion site of the foreign gene, but the insertion of the foreign gene as a gene cassette containing gene expression regulatory sequences is preferable for the same reason as described above, in order to permit the expression of the foreign gene to be regulated more suitably and efficiently. In this case, the gene expression regulatory sequences such as a promoter etc. include the gC promoter and gB promoter derived from FHV-1, the IE promoter from human cytomegalovirus and the RNA 1.8 promoter derived from MDV. Among these, the gC promoter and the IE promoter from human cytomegalovirus are particularly preferable for the same reason as described above.

Each of the foreign genes inserted into two different gene regions in the feline herpesvirus type 1 in such a manner as to allow the expression are characterized by being: a gene derived from pathogenic microorganisms and encoding a polypeptide inducing an ability to protect animals from infection, or a gene fragment consisting of a part of the gene; or a gene derived from various cytokines such as interferon $\gamma$, interferon $\alpha$, interferon $\beta$, interferon $\omega$, interleukin 12, interleukin 18, interleukin 10 and TNF$\alpha$ and encoding a product exhibiting a therapeutic effect on animals, or a gene fragment consisting of a part of the gene.

This invention also encompasses a vaccine or a therapeutic composition comprising the above-described attenuated feline herpesvirus type 1, and the vaccine or the therapeutic composition is characterized by being used in inoculation via the mucosa.

Further, this invention encompasses a method of preparing an attenuated recombinant feline herpesvirus type 1 having at least two types of foreign genes inserted in such as a manner as to allow the expression into two different gene regions of the feline herpesvirus type 1 genome. This preparation method is characterized by comprising (1) the step of preparing at least two types of transfer vectors comprising different foreign genes capable of expression inserted into a gene fragment consisting of two different gene regions in the feline herpesvirus type 1 genome, (2) the step of using at least two types of transfer vectors thus obtained, to introduce the gene fragment consisting of different gene regions into which the foreign genes were inserted in the feline herpesvirus type 1 genome, into feline cells preferably established feline cell lines, and simultaneously infecting the cells with feline herpesvirus type 1, to cause homologous genetic recombination between the introduced gene fragment and the feline herpesvirus type 1 genome, and (3) the step of selecting the feline herpesvirus type 1 which has undergone homologous genetic recombination. In this method, the homologous genetic recombination between a plurality of the introduced gene fragments and the feline herpesvirus type 1 genome is conducted in one procedure.

The attenuated recombinant feline herpesvirus type 1 of the invention can also be obtained by superinfection of feline cells, preferably established feline cell lines, with recombinant viruses having foreign genes inserted into different regions of the genome. This preparation method is characterized by comprising (1) the step of preparing at least two types of transfer vectors comprising different foreign genes capable of expression inserted into a gene fragment consisting of two different gene regions in the feline herpesvirus type 1 genome, (2) the step of using at least two types of transfer vectors thus obtained, to introduce the gene fragment consisting of different gene regions into which the foreign genes were inserted in the feline herpesvirus type 1 genome, into feline cells preferably established feline cell lines, and simultaneously infecting the cells with feline herpesvirus type 1, to cause homologous genetic recombination between the introduced gene fragment and the feline herpesvirus type 1 genome, (3) the step of selecting the feline herpesvirus type 1 which has undergone homologous genetic recombination, to obtain at least two types of recombinant feline herpesviruses type 1 wherein one gene region in the feline herpesvirus type 1 genome has undergone recombination, (4) the step of superinfection of feline cells preferably established feline cell lines, with the respective recombinant feline herpesviruses type 1 thus obtained, to cause homologous genetic recombination between the genomes of at least two types of the recombinant feline herpesviruses type 1, and (5) the step of selecting the feline herpesvirus type 1 which has undergone homologous genetic recombination. This method comprises the step of preparing and isolating at least two types of recombinant feline herpesviruses type 1 having foreign genes inserted into one gene region in the feline herpesvirus type 1 genome.

The cells to be infected with the feline herpesvirus type 1 refer to cells derived from cats. The established feline cell lines are those cells consisting of a single cell species and characterized by being capable of continuous culture by tissue culture techniques. Such established feline cell lines include, for example, CrFK cells that are established cells derived from the feline kidney(R. A. Crandell et al., 1973, In Vitro 9: 176-185), MYA-1 cells that are an interleukin 2-dependent lymphocyte line (T. Miyazawa et al., 1989, Arch. Virol. 108: 131-135), Fet-J cells that are an interleukin-independent CD4-positive lymphocyte line (T. Hohdatsu et al., 1996, J. Gen. Virol. 77: 93-100) etc. Among these cells, CrFK cells are preferable in respect of high sensitivity to FHV-1 and good proliferation of FHV-1.

In the method of preparing the feline herpesvirus type 1, the two different gene regions in the feline herpesvirus type 1 genome, into which foreign genes are inserted, are preferably two gene regions, that is, an I fragment region present in the unique long ($U_L$) region out of SalI digested DNA fragments of the feline herpesvirus type 1 genome and a gene region encoding thymidine kinase, or two gene regions, that is, a gene region encoding protein kinase present in the unique long ($U_L$) region in the feline herpesvirus type 1 genome and a gene region encoding thymidine kinase.

Further, this invention provides a method of expressing or producing foreign genes in cells by infecting cells with the thus obtained attenuated feline herpesvirus type 1 used as a vector, as well as a method of giving immunity to animals by inoculating it as a polyvalent vaccine into animals via the mucosa.

The cells to be infected are preferably those having a receptor for the feline herpesvirus type 1. Such cells are cells derived from cats, preferably established feline cell lines. The animals to be inoculated with the vaccine are preferably animals of the Felidae, preferably animals such as cats capable of immunization with the feline herpesvirus type 1. The immunity to be given includes not only general humoral immunity and cellular immunity but also local immunity based on inoculation via the mucosa. On one hand, animals other than those of the Felidae can also be endowed with immunity by inoculating the recombinant feline herpesvirus type 1 of the invention as a vaccine. That is, non-feline animals insensitive to the feline herpesvirus type 1, upon inoculation with the recombinant feline herpesvirus type 1, can express and produce at least the foreign genes inserted into the FHV-1 genome. As a result, when the foreign genes encode antigenic proteins of pathogenic microorganisms, the inoculated animal is endowed with immunity to the pathogenic microorganisms.

As described above, the inventors found new insertion sites for foreign genes, by which a new FHV-1 vector capable of inserting foreign genes into two gene regions in the FHV-1 genome, which has not been reported up to now, was created.

From the foreign genes to be inserted into two different regions in the feline herpesvirus type 1 genome, a gene encoding a polypeptide inducing an ability to protect animals from infection or a gene fragment consisting of a part of the gene includes a gene encoding an antigenic protein produced by various microorganisms infecting animals of the cat family, mainly cats, or a gene fragment consisting a part of the gene and a gene encoding an antigenic protein produced by various pathogenic microorganisms infecting animals other than cats. Examples thereof include genes encoding an envelope protein and core protein of feline leukemia virus, VP2 protein of feline pan-leucopoenia virus, an envelope protein and core protein of feline immunodeficiency virus, a capsid protein of feline calicivirus, a major outer membrane protein MOMP-1 of chlamydiales, an envelope protein and nucleotide capsid protein of rabies virus, and a structural protein of canine distemper virus or canine parvovirus, or gene fragments consisting a part thereof.

A gene encoding a gene product showing a therapeutic effect on animals, or a gene fragment consisting of a partial sequence of the gene, includes genes encoding cytokine types TH1 and TH2 showing a protecting effect and a therapeutic effect in cats or other animals against viral infections, microbial infections or tumors. Examples thereof include genes encoding interferon $\gamma$, interferon $\alpha$, interferon $\beta$, interferon $\omega$, interleukin 12, interleukin 18, interleukin 10 and TNF$\alpha$ or gene fragments consisting of a part thereof.

This invention encompasses the disclosure of Japanese Patent Application No. 2000-306802 (filing date: Oct. 5, 2000) whose disclosure is incorporated herein by reference.

BRIEF DESCRIPTION OF DRAWINGS

FIG. 1 is a drawing showing the feline herpesvirus type 1 genome and a map of the genome upon digestion with SalI. This drawing also shows conventionally known insertion regions for foreign genes, together with the insertion regions for foreign genes and the sequence region in this invention.

FIG. 2 is an illustration of the insertion sites in the recombinant FHV-1 genome of this invention.

FIG. 3 is a drawing showing an outline of the method of preparing a transfer vector (pdBSI-LacZ) having LacZ inserted thereinto.

FIG. 4 is a drawing showing an outline of the method of preparing the recombinant FHV-1 having a LacZ/FCV capsid gene inserted thereinto.

FIG. 5 is an illustration of the constructed transfer vector pdBSI-LacZ.

FIG. 6 is a photograph showing the analysis results of various plasmid vectors by agarose gel electrophoresis.

FIG. 7 is an illustration showing the structure of the transfer vector pfTK (gCp)-Cap having a feline calicivirus capsid protein gene and FHV-1-derived gC promoter integrated therein, which was used in construction of dTK-gC/Cap-FHV i.e. the recombinant FHV-1 having the TK-defective feline calicivirus capsid protein gene inserted thereinto.

FIG. 8 is a photograph showing the detection results of $\beta$ galactosidase and FCV capsid protein in CrFK cells infected with FHV-Cap/Lac by the indirect immunofluorescence assay. In the photograph, A indicates the result of $\beta$ galactosidase ditected with FITC, and B indicates the result of FCV capsid labeled with TRITC.

FIG. 9 is a photograph showing the detection results of $\beta$ galactosidase antibody in serum from a cat inoculated with FHV-Cap/Lac by the indirect immunofluorescence assay using feline serum as primary antibody on day 5 after boost with FHV-Cap/Lac and FITC-labeled goat anti-cat IgG antibody as secondary antibody. In the photograph, A indicates the result of CrFK cells into which pCMV$\beta$ DNA was not transfected (negative control), while B indicates the result of CrFK cells into which pCMV$\beta$ DNA was transfected.

FIG. 10 is a photograph showing the detection results of anti-calicivirus capsid protein antibody by the indirect immunofluorescence assay. In the photograph, A indicates the result of a negative control wherein the serum of a cat before inoculation with FHV-Cap/Lac was reacted with CrFK cells infected with feline calicivirus, while B indicates the result of the reaction of the serum of a cat inoculated with FHV-Cap/Lac with CrFK cells infected with feline calicivirus.

FIG. 11 shows comparison of an amino acid sequence deduced form a nucleotide sequence (PstI-HindIII DNA fragment) in the vicinity of the BamHI-digested site in the SalI fragment present on the $U_L$ region of the FHV-1 (SEG ID NO:2) genome of this invention, with an amino acid sequence of the protein kinase present in the $U_L$-region of each of herpes simplex virus type 1 (HSV-1) (SEQ ID NO:9), equine herpes virus type 1 (EHV-1) (SEQ ID NO:10) and equine herpesvirus type 4 (EHV-4) (SEQ ID NO: 11). In the figure, the region enclosed with the square indicates each of catalytic domains I to VI in protein kinase, and "*" shows that the amino acid in FHV-1, indicated by this symbol, is identical with an amino acid in any one of HSV-1, EHV-1 or EHV-4.

BEST MODE FOR CARRYING OUT THE INVENTION

The attenuated recombinant feline herpesvirus type 1 of this invention comprises at least two types of foreign genes inserted in such a manner as to allow the expression into two different gene regions in the feline herpesvirus type 1 genome, and can be used as a vector or a vaccine.

The recombinant virus can be obtained by preparing different transfer vectors and subsequent homologous genetic recombination between the transfer vector gene sequences and the feline herpesvirus type 1 genome. That is, the feline herpesvirus type 1 having foreign genes inserted into two different regions in the genome, as shown in this invention, can be obtained by causing homologous genetic recombination between two types of transfer vectors and two regions in the genome, or by first preparing feline herpesviruses type 1, each having a foreign gene inserted into a different region in the genome and subsequent superinfection of these viruses to cause homologous genetic recombination. The latter is a preferable method in that the respective recombinant viruses are proliferated in the infected cells, to increase the probability of homologous genetic recombination.

The regions into which foreign genes is inserted, is not regions encoding a gene essential for proliferation of the virus, but regions capable of expressing the inserted foreign genes. The foreign gene insertion regions satisfying this requirement include, for example, two gene regions, that is, the I fragment region present in the unique long ($U_L$) region out of SalI digested DNA fragments of the feline herpesvirus type 1 genome and a gene region encoding thymidine kinase, or two gene regions, that is, a gene region encoding protein kinase present in the unique long ($U_L$) region in the feline herpesvirus type 1 genome and a gene region encoding thymidine kinase.

When a foreign gene is to be inserted into the I fragment region, the insertion region for the foreign gene may be any part of the I fragment. In particular, the region shown in SEQ ID NO:1 (sequence region, PstI-HindIII in the I fragment, FIG. 1) which is a determined partial sequence of the I fragment is a preferable region because the foreign gene can be easily inserted into this region.

In the case where a foreign gene is to be inserted into a gene region encoding protein kinase, the protein kinase is encoded by a gene sequence in the I fragment region, and contains the amino acid sequence set forth in SEQ ID NO:2 as a part thereof. Accordingly, the insertion region for the foreign gene may be not only a structural gene encoding protein kinase but also a regulatory gene region for protein kinase, and can be not only the I fragment region but also the whole gene encoding protein kinase.

Maps of the feline herpesvirus type 1 genome and the genome digested with SalI, together with conventionally known insertion regions for foreign genes, are shown in FIG. 1. In the figure, $U_L$ refers to the unique long region, $U_S$ to the unique short region, $IR_S$ to the internal repeat short region, and $TR_S$ to the terminal repeat short region. Each of the letters A to N refers to a name of each fragment obtained by cleavage with SalI (P. A. Rota et al., 1986, Virology 154: 168-179; A. Grail et al., 1991, Arch. Virol. 116: 209-220). As particularly preferable insertion sites for foreign genes in this invention, one site is the sequence region in the I fragment, particularly the BamHI site, and the other site is the thymidine kinase region shown by TK in the A fragment.

When a gene sequence in the vicinity of the BamHI site as a unique insertion site for a foreign gene in the I fragment was examined, the gene sequence was found to constitute a part of the gene sequence encoding protein kinase. Accordingly, the gene region encoding protein kinase is preferable as an insertion site for a foreign gene.

Each of foreign genes inserted into these regions has been confirmed to express a protein as a gene product in the infected cells. In addition, the recombinant FHV-1 constructed in this invention is a virus rendered further attenuated (nonpathogenic) by deleting the thymidine kinase of attenuated FHV-1 used for preparation of the recombinant virus.

Accordingly, the attenuated feline herpesvirus type 1 of this invention can be used as a vector or a vaccine. When used as a vaccine, the attenuated feline herpesvirus type 1 has been confirmed to induce production of antibodies to proteins produced by expression of at least two types of inserted foreign genes and an antibody to the feline herpesvirus type 1. Further, this vaccine is a herpesvirus, so it is administered preferably via the mucosa, that is, orally or via the nose or as eye drops, but conventional administration by injection is also effective.

The vaccine can be prepared by suspending the recombinant FHV-1 of this invention in an isotonic phosphate buffer. The amount of the virus inoculated into an animal varies depending on the titer and immunogenicity of the virus, for example, in the case of inoculation into a cat via the mucosa, the amount of the vaccine solution administered is generally 1 to 2 ml. The amount of the virus is regulated preferably such that immunity can be induced by the amount of the solution administered.

Hereinafter, one example of this invention wherein a gene fragment encoding a feline calicivirus capsid protein and a gene encoding β galactosidase were used as foreign genes is described.

As illustrated in FIG. 2, the recombinant FHV-1 (FHV-Cap/Lac, see FIG. 2C) has the gC-Cap fragment and the Pro-LacZ fragment integrated in the same viral genome, which is obtained through viral homologous genetic recombination by a superinfection of feline kidney-established cells with: recombinant FHV-1 (dTK-gC/Cap-FHV, FIG. 2A, see JP-A 9-267) wherein a gene fragment (gC-Cap) encoding a feline calicivirus (FCV) capsid protein, accompanied by glycoprotein C promoter (gC promoter) derived from FHV-1, was integrated in the defective TK site of known TK-defective FHV-1; and recombinant FHV-1 (Lac FHV, FIG. 2B) wherein β galactosidase gene (Pro-LacZ) fragment, accompanied by an IE promoter derived from Human cytomegalovirus (CMV), was integrated in the I fragment of FHV-1.

Hereinafter, the method of preparing the recombinant FHV-1 is described.

First, a transfer vector containing the Pro-LacZ fragment was constructed in the following manner. That is, a plasmid vector pSal-I (obtained from Dr. T. Miyazawa, Department of Agriculture, Tokyo University) wherein the I fragment as one of the SalI digested DNA fragments of the FHV-1 genome DNA had been integrated was cloned again in a commercial plasmid vector whose BamHI recognition site had been deleted, and then a LacZ gene fragment (Pro-LacZ) accompanied by an IE promoter derived from a commercial eucaryotic cell expression vector pCMVβ (CLONETECH) was integrated in a unique BamHI cleavage site in the newly constructed plasmid pdBSI containing the I fragment, to prepare a transfer vector pdBSI-LacZ.

*E. coli* as a transformant containing the pdBSI-LacZ was deposited on Jun. 30, 2000 as E-dBSI-LacZ (FERM P-17935) with the International Patent Organism Depositary (IPOD), National Institute of Bioscience and Human-Technology (NIBH), the Agency of Industrial Science and Technology, the Ministry of International Trade and Industry, Japan and transferred to international deposition (accession number FERM BP-7761) on Oct. 3. 2001. At present, the name of the depositary has been changed to “International Patent Organism Depositary (IPOD), National Institute of Advanced Industrial Science and Technology (AIST)”.

From the transformant E-dBSI-LacZ constructed in the manner described above, pdBS-LacZ DNA was extracted and introduced by transfection into CrFK cells (Crandell feline kidney cells i.e. feline kidney-derived established cells, obtained from Dr. T. Miyazawa, Department of Agriculture, Tokyo University), and the CrFK cells were infected with attenuated FHV-1. Thereafter, homologous genetic recombination was caused between the I fragment derived from the FHV-1 genome DNA in pdBSI -LacZ and the FHV-1 genome DNA, to prepare recombinant FHV-1 having Pro-LacZ inserted into the I fragment region of FHV-1. The recombinant FHV-1 thus prepared was designated LacZ-FHV (FIG. 2B).

Then, the EcoRV-SmaI gene fragment in the TK gene region was deleted from the FHV-1 genome by genetic engineering technology, and then recombinant FHV-1 (dTK-gC/Cap-FHV, FIG. 2A, obtained from Dr. T. Miyazawa, Department of Agriculture, Tokyo University; see N. Yokoyama et al., 1998, J. Vet. Med. Sci. 60: 717-723) wherein a DNA fragment links with FHV-1-derived gC promoter and a gene encoding FVC capsid protein had been inserted into the above deleted site, and the above LacZ-FHV, were used to co-infect CrFK cells, to cause homologous genetic recombination between these two recombinants FHV-1, to prepare recombinant FHV-1 having LacZ inserted into the BamHI site in the I fragment of the FHV-1 genome and the FCV capsid protein gene inserted into the TK gene region.

The desired final recombinant FHV-1 obtained in this manner, that is, the recombinant FHV-1 capable of producing FCV capsid protein and β galactosidase, was designated FHV-Cap/LacZ (FIG. 2C).

These procedures can be carried out by known genetic manipulation techniques and cellular engineering techniques described by Sambrook et al. (J. Sambrook et al., 1989, Molecular cloning: a laboratory manual. 2nd edition, Cold Spring Harbor, N.Y.: Cold Spring Harbor Press).

The FHV-Cap/LacZ thus obtained had the ability to be replicated in a cell lines derived from cats and in cats, and upon inoculation into the nasal cavity, eyes or oral cavity of a cat, the cat did not show any clinical sign, and thus its safety to the cat was confirmed.

In this invention, it was found for the first time that as shown above, the BamHI recognition site in the I fragment located in the $U_L$ region out of SalI digested DNA fragments of the FHV-1 genome is not essential for replication of FHV-1, and also that after a foreign gene is integrated into the I fragment, a gene product of the integrated foreign gene is produced in cells derived from animals and in animal bodies.

In this invention, the recombinant FHV-1 having foreign genes integrated into two gene regions, that is, into the TK gene and the I fragment present in the $U_L$ region out of SalI digested DNA fragments of the FHV-1 genome was constructed for the first time, and the replication of the recombinant FHV-1 in a cell line derived from cats and in cat bodies was found for the first time.

Further, a nucleotide sequence in the vicinity of the BamHI-digested site in the Sal I fragment, found first as an insertion site for a foreign gene, was determined, and an amino acid sequence deduced from the nucleotide sequence was analyzed, and as a result, it was found that the sequence in the vicinity of the BamHI-digested site maintains almost the same amino acid sequence as that of catalytic domains I to VI of protein kinase in another herpesvirus. The nucleotide sequence of the SalI I fragment in the FHV-1 genome has not been determined so far, and it was found for the first time in this invention that the nucleotide sequence encoding protein kinase is present in the I fragment.

Further, it was found for the first time in this invention that the protein kinase region in the $U_L$ region of the FHV-1 genome is effective as an insertion site for a foreign gene.

Hereinafter, this invention is described in more detail by reference to the Examples. FIGS. 3 and 4 show an outline of experimental procedures carried out in this invention. FIG. 3 shows an outline of procedures prior to construction of a LacZ-inserted transfer vector pdBSI-LacZ, and FIG. 4 shows an outline of the method of preparing FHV-Cap/Lac as recombinant FHV-1 having LacZ and FCV capsid genes inserted thereinto by using DNA from the transfer vector pdBSI-LacZ.

EXAMPLE 1

Construction of a Transfer Vector for Construction of a Recombinant FHV-1 Vector (1) Construction of a Plasmid for Integration of the FHV-1 Genome I Fragment pSal-I (obtained by Dr. T. Miyazawa, Department of Agriculture, Tokyo University) which is a plasmid vector containing the I fragment from a SalI library of FHV-1 genome DNA was digested with SalI, and using a commercial QIAquick Gel Extraction Kit (manufactured by QIAGEN), the fragment I of FHV-1 genome was separated and prepared according to its attached manual.

Separately, as a plasmid vector for integration of the fragment I, a commercial plasmid vector pUC18 (manufactured by Amersham Pharmacia Biotech) ring-opened by digestion with BamHI was blunt-ended by incubation at 37° C. for 5 minutes in the presence of T4 DNA polymerase (manufactured by Takara Shuzo Co., Ltd.). Thereafter, the site blunt-ended with BamHI was ligated by incubation at 16° C. for 17 hours in the presence of T4 DNA ligase (manufactured by GIBCO BRL). The resulting plasmid vector deficient in the BamHI recognition site was designated pUC-dB. In the drawing, the BamHI enclosed with the square indicates the BamHI site eliminated by this procedure.

Then, pUC-dB was ring-opened by digestion with SalI, and the FHV-1 genome I fragment separated and prepared above was ligated by T4 DNA ligase to the site digested with SalI. The thus obtained plasmid having the FHV-1 genome I fragment integrated in the SalI-digested site of pUC-dB was designated pdBSI.

(2) Preparation of a Transformant Containing pdBSI

A pdBSI DNA solution was mixed with commercial competent *E. coli* XL-1 Blue (manufactured by Stratagene), and according to its attached manual, the plasmid DNA was introduced into *E. coli*, whereby the *E. coli* was transformed. Further, the transformant was cultured at 37° C. for 17 hours in an LB agar medium containing 50 μg/ml ampicillin (agar medium containing 10 g Bactotrypton, 5 g Bactoyeast extract, 10 g sodium chloride and 15 g Bactoagar per 1 L), whereby ampicillin-resistant transformed clones proliferated on the agar medium were obtained. The plasmid DNA extracted from each of the transformed clones was digested with SalI and analyzed by electrophoresis on 0.8% agarose gel (FIG. 6, lane 1), and a transformed clone having the about 6,800-bp fragment I was selected and this clone was named E-dBSI.

(3) Construction of a Transfer Vector

As a commercial eucaryotic cell expression plasmid vector, β-galactosidase-expressing pCMVβ (manufactured by CLONETECH) was digested with PstI, and the gene fragment (Pro-LacZ) containing the LacZ gene accompanied by an IE promoter derived from CMV was isolated and purified by using the above-mentioned QIAquick Gel Extraction Kit. Thereafter, the Pro-LacZ was incubated at 37° C. for 5 minutes in the presence of T4 DNA polymerase, whereby the PstI-digested site was blunt-ended.

Separately, as a plasmid for integration of Pro-LacZ, the above pdBSI having one BamHI recognition site in the I fragment was ring-opened with BamHI, and the BamHI site was blunt-ended by treatment with T4 DNA polymerase in the same manner as described above.

Figure 3:
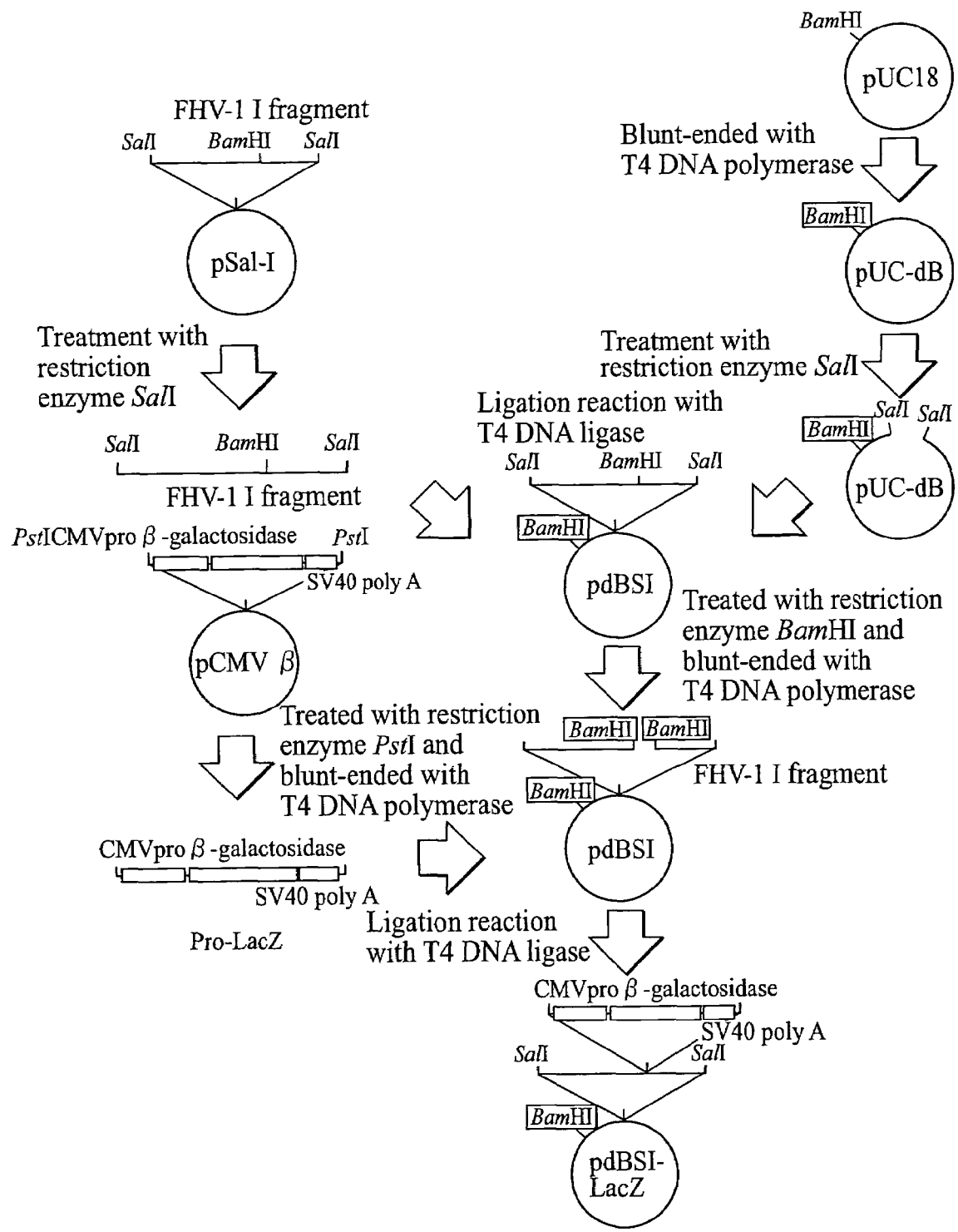

Then, the blunt-ended Pro-LacZ was ligated with the ring-opened and blunt-ended pdBSI by incubation at 16° C. for 17 hours in the presence of T4 DNA ligase. The resulting transfer vector having Pro-LacZ integrated into the blunt-ended BamHI site of the I fragment in the FHV-1 genome-derived SalI library was designated pdBSI-LacZ (FIG. 3).

Figure 5:
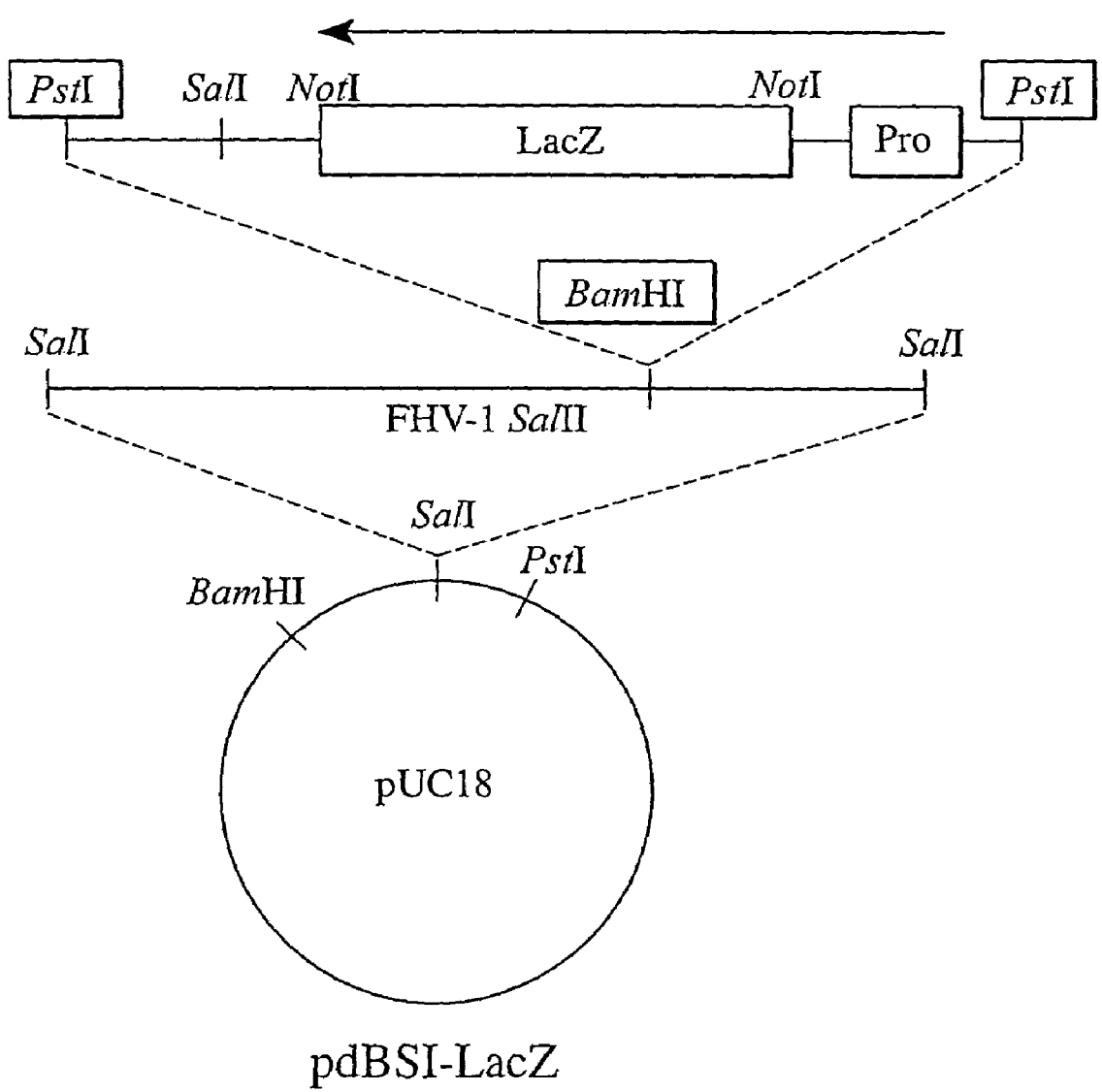

An outline of the constructed transfer vector pdBSI-LacZ is shown in FIG. 5. In the figure, "LacZ" refers to the LacZ gene fragment; and PstI and BamHI enclosed with the square refer to the PstI recognition site and BamHI recognition site which were blunt-ended respectively; "Pro" refers to the IE promoter of human cytomegalovirus (HCMV); and the arrow indicates the direction of the LacZ gene fragment and the promoter.

EXAMPLE 2

Preparation of a Transformant Containing pdBSI-LacZ

A pdBSI-LacZ DNA solution was mixed with a commercial competent *E. coli* XL-2 Blue MRF', and the plasmid DNA was transformed into the *E. coli* according to its attached manual, and the transformant was cultured at 37° C. for 17 hours in an LB agar medium containing 50 µg/ml ampicillin to provide ampicillin-resistant transformant clones which proliferated on the agar medium.

Figure 6:
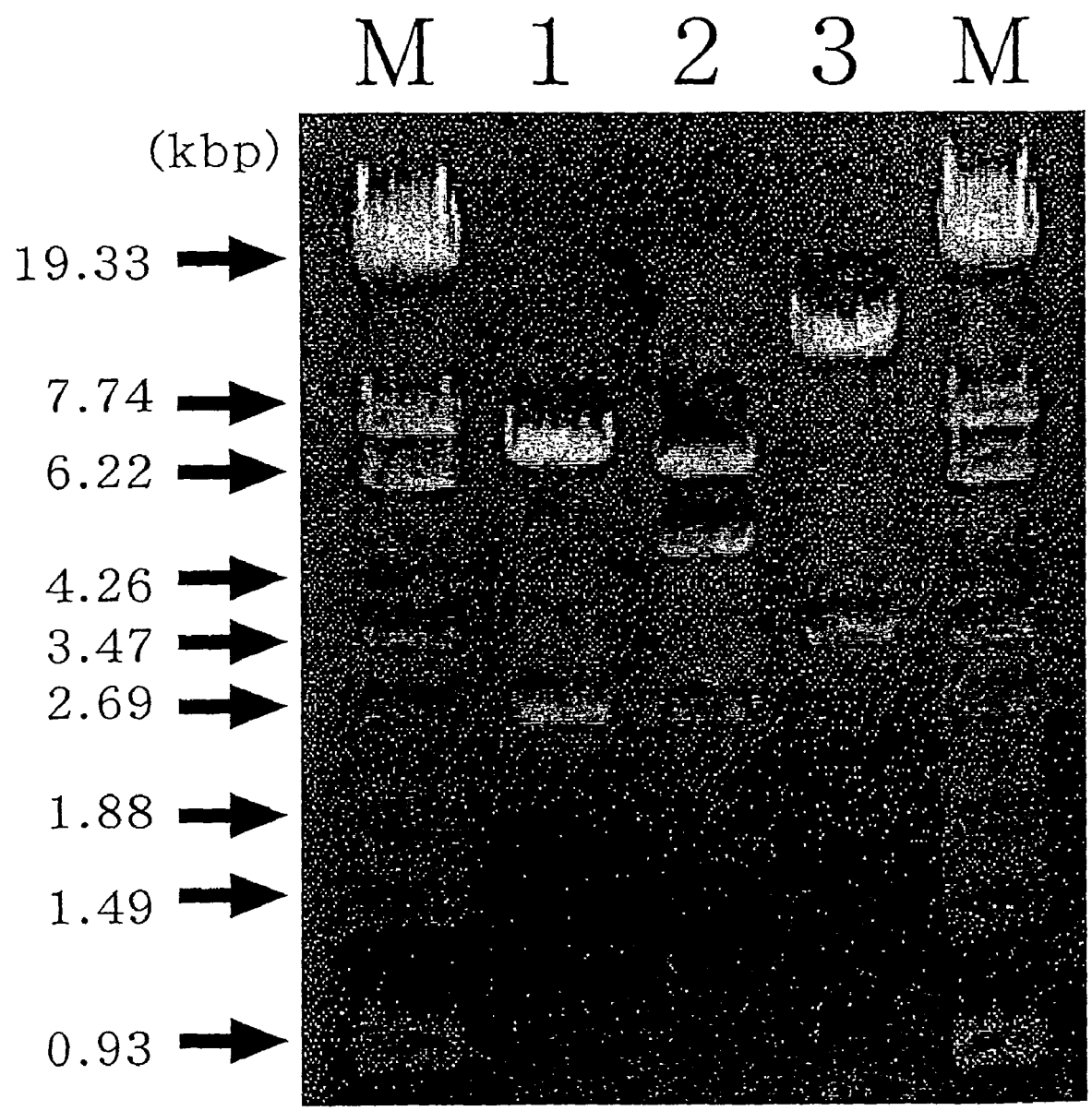

Then, the plasmid DNA extracted from each of the transformant clones was digested with SalI and analyzed by electrophoresis on 0.8% agarose gel, whereby a clone having both the I fragment divided into two fragments of about 6,600 base pairs and about 4,700 base pairs (based on the SalI site in the Pro-LacZ cassette inserted into the I fragment, see FIG. 5) and a vector plasmid pUC18 DNA fragment of about 2,600 base pairs was selected (FIG. 6, lane 2, digestion of pdBSI-LacZ with SalI). By digestion of the selected clone with NotI, the clone was confirmed to have a LacZ DNA fragment of 3,474 base pairs (FIG. 6, lane 3, digestion of pdBSI-LacZ with NotI). In the results of electrophoresis shown in FIG. 6, lane 1 shows SalI-digested pdBSI into which the I fragment not containing Pro-LacZ was inserted, and the presence of two fragments i.e. the I fragment of about 7,000 base pairs and a vector plasmid pUC18 DNA fragment of about 2,600 base pairs is confirmed (see FIG. 5). In FIG. 6, lane M shows molecular-weight markers each indicating an approximate number of base pairs.

The thus selected *E. coli* transformed with the transfer vector pdBSI-LacZ was designated E-dBSI-LacZ and deposited with the International Patent Organism Depositary (IPOD), the National Institute of Bioscience and Human-Technology (NIBH), the Agency of Industrial Science and Technology, the Ministry of International Trade and Industry, Japan, (Accession No. FERM P-17935) and transferred to International Deposition on Oct. 3, 2001 (Accession No. FERM BP-7761).

EXAMPLE 3

Preparation of Recombinant FHV-1 into which LacZ was Inserted

The above transfer vector pdBSI-LacZ DNA was introduced by transfection into CrFK cells, and the CrFK cells into which the gene had been introduced were infected with attenuated FHV-1, followed by homologous genetic recombination between pdBSI-LacZ DNA and attenuated FHV-1 genome in the cells, to obtain the recombinant FHV-1 having the LacZ gene integrated into the BamHI digested site in the I fragment as one of the SalI digested DNA fragments of the FHV-1 genome. Hereinafter, this is described in more detail.

3 µg pdBSI-LacZ DNA was mixed with 10 µl of a commercial transfection reagent LipofectAMINE (manufactured by GIBCO BRL), and the mixture was incubated at room temperature for 45 minutes. Then, $1 \times 10^6$ CrFK cells, which had been cultured at 37° C. in Dulbecco's minimum essential medium (abbreviated hereinafter into D-MEM, manufactured by Nissui) containing 10% fetal bovine serum in a 6-wells tissue culture plate in the presence of 5% carbon dioxide gas and then washed twice with 3 ml D-MEM, were supplemented with the above reaction solution containing the pdBSI-LacZ DNA and the transfection reagent, to introduce the pdBSI-LacZ DNA into the CrFK cells.

Then, the CrFK cells into which the gene had been introduced were cultured at 37° C. in the presence of 5% carbon dioxide gas for 24 hours, and the CrFK cells were infected with attenuated FHV-1 in a MOI (multiplicity of infection) of 0.01. After introduction of the pdBSI-LacZ DNA in this manner, the CrFK cells infected with the attenuated FHV-1 were cultured for about 3 days, and when almost all cells were recognized to have a cytopathic effect (abbreviated hereinafter as CPE), the cell suspension was frozen and thawed 3 times to disrupt the cells, and a viral liquid containing both the attenuated FHV-1 and recombinant FHV-1 was finally recovered in a centrifuged supernatant of the disrupted cell solution. The screening of the recombinant FHV-1 from this viral liquid was conducted by the following plaque selection assay.

That is, the recovered viral liquid was diluted stepwise from $10^{-1}$ to $10^{-5}$ with D-MEM, and each diluted viral liquid, 300 µl, was added to the $1 \times 10^6$ CrFK cells proliferated in a 6-wells tissue culture plate, then the virus was adsorbed into the cells at 37° C. for 1 hour, and 1 ml D-MEM soft agar medium containing 2% fetal bovine serum and 1% agarose was layered on the cells. The cells were then cultured for 2 days. Then, 1 ml D-MEM soft agar medium containing 0.01% neutral red, 1 mg/ml X-gal (5-bromo-4-chloro-3-indolyl-β-D-galactopyranoside, manufactured by SIGMA), 1% fetal bovine serum and 1% agarose was layered thereon, and the cells were cultured for additional 24 hours, then blue plaques formed by the proliferated recombinant virus were separated. Hereinafter, the same plaque assay was repeated twice, to select the recombinant FHV-1 having LacZ inserted into the I fragment in the genome. The recombinant FHV-1 having LacZ inserted thereinto was designated Lac-FHV (see FIG. 2B).

EXAMPLE 4

Preparation of Recombinant FHV-1 into which LacZ and FCV Capsid Protein Gene were Inserted (1) Preparation of TK-Defective FHV-1 into which a FCV Capsid Protein Gene was Inserted A recombinant FHV-1 (dTK-gC/Cap-FHV, obtained from Dr. T. Miyazawa, Department of Agriculture, Tokyo University) comprising an FCV capsid protein gene, accompanied by a FHV-1-derived gC promoter, inserted into the TK gene region was added to $1\times10^7$ CrFK cells in a MOI of 0.01 in a tissue culture flask, followed by adsorption and infection at 37° C. for 1 hour. Then, the cells were cultured in D-MEM medium containing 2% fetal bovine serum at 37° C. in the presence of 5% carbon dioxide gas for about 3 days until CPE was recognized in almost all cells. Subsequently, the cell suspension was frozen and thawed 3 times, to disrupt the cells, and recombinant FHV-1 having the FCV capsid protein gene inserted into the defective TK gene region was obtained in a centrifuged supernatant of the disrupted cell solution. The recombinant FHV-1 thus obtained was designated dTK-gC/Cap-FHV (see FIG. 2A).

Figure 7:
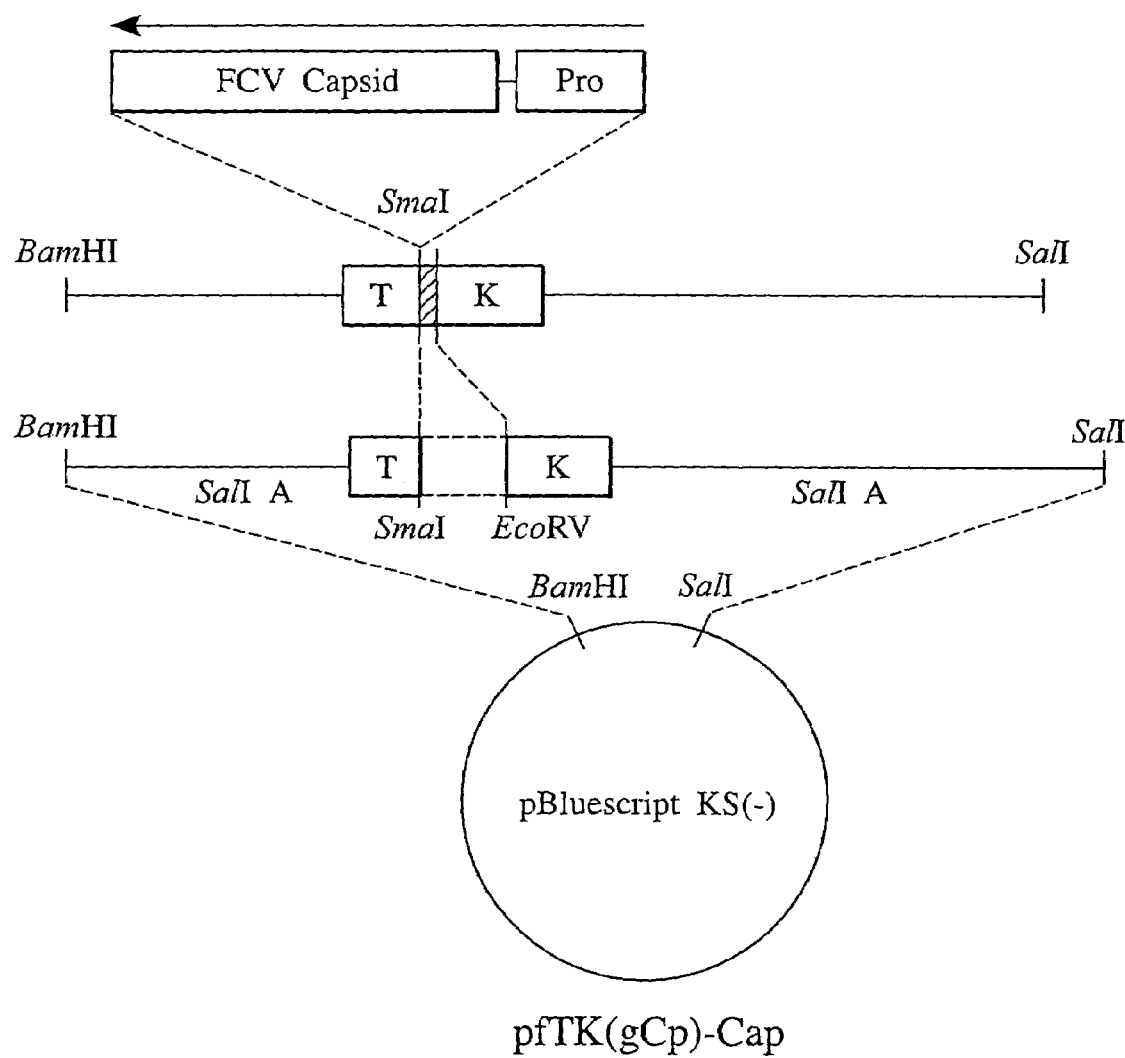

The transfer vector (designated pfTK(gCp)-Cap) having the feline calicivirus capsid protein gene and FHV-1-derived gC promoter integrated therein, which was used in constructing dTK-gC/Cap-FHV as recombinant FHV-1, has a structure shown in FIG. 7, wherein the shaded region in the figure indicates a part of a multicloning site derived from a plasmid vector (pBluescript KS-) integrated for construction of pfTK(gCp)-Cap; "Pro" refers to the gC promoter derived from FHV-1; "FCV Capsid" to the feline calicivirus capsid protein gene; "SalI A" to a A fragment of SalI digestes derived from the FHV-1 genome; and "TK" to a thymidine kinase gene; and the region indicated by the dotted lines in the thymidine kinase gene ("TK") refers to the deleted gene region. The arrow in the figure indicates the direction of the feline calicivirus capsid gene and the promoter.

(2) Preparation of FHV-Cap/Lac

Lac-FHV was added in a MOI of 0.01 to $1\times10^6$ CrFK cells in a 6-wells tissue culture plate, and by incubation at 37° C. for 1 hour, the CrFK cells were infected through adsorption with the recombinant virus, and then the CrFK cells infected with Lac-FHV were proliferated by culture for 24 hours in a D-MEM medium containing 2% fetal bovine serum. Then, dTK-gC/Cap-FHV viral liquid was added in a MOI of 0.01 to the CrFK cells infected with Lac-FHV, and the CrFK cells infected with Lac-FHV were superinfected through adsorption with dTK-gC/Cap FHV in the same manner as above. The cells superinfected with Lac-FHV and dTK-gC/Cap-FHV were cultured for about 3 days until CPE was recognized, then the cells were disrupted by freezing and thawing in the same manner as above, and a virus liquid containing the recombinant virus, that is, the recombinant FHV-1 having the LacZ gene and FCV capsid protein gene, accompanied by gC promoter, integrated in one virus genome by partial genetic recombination between Lac-FHV and dTK-gC/Cap-FHV, was obtained in a centrifuged supernatant of the disrupted cell solution. Selection of the recombinant FHV-1 from the viral liquid was conducted by the following plaque assay.

That is, the viral liquid was diluted stepwise from $10^{-1}$ to $10^{-5}$, and each diluted viral liquid, 300 μl, was added to $1\times10^6$ CrFK cells in a 6-wells tissue culture plate, and the cells were infected through adsorption with the virus at 37° C. for 1 hour, and 1 ml D-MEM soft agar medium containing 100 mg arabinofuranocyluracil, 2% fetal bovine serum and 1% agarose was layered on the proliferated CrFK cells adhering to the bottom of the culture plate, and the cells were cultured at 37° C. in the presence of 5% carbon dioxide gas. After 2 days, on the D-MEM soft agar medium, 1 ml D-MEM soft agar medium containing 0.01% neutral red, 1 mg/ml X-gal, 100 mg arabinofuranocyluracil, 1% fetal bovine serum and 1% agarose was layered, and the cells were further cultured. After 24 hours, blue plaques formed by the proliferated recombinant virus were isolated. Hereinafter, the plaque assay was repeated twice in the same manner as described above, to select the recombinant FHV-1 having the LacZ gene inserted into the I fragment of the genome and the FCV capsid protein gene accompanied by FHV-1-derived gC promoter inserted into the deleted TK gene region. The recombinant FHV-1 thus obtained was designated FHV-Cap/Lac (see FIG. 2C).

The resulting FHV-Cap/Lac was issued with a certificate of rejection of deposition dated Dec. 2, 1999 (filed on Nov. 29, 1999) by the International Patent Organism Depositary (IPOD), National Institute of Bioscience and Human-Technology (NIBH), the Agency of Industrial Science and Technology, the Ministry of International Trade and Industry, so the recombinant virus FHV-Cap/Lac is not deposited with the above depositary, but is conserved in the central laboratory in Kyoritsu Seiyaku, Corporation and can be distributed if necessary. At present, we are planning to deposit the FHV-Cap/Lac with the ATCC (American Type Culture Collection).

EXAMPLE 5

Expression of Foreign Proteins from FHV-Cap/Lac in a Established Cell Strain

The expression of FCV capsid protein and β-galactosidase derived from FHV-Cap/Lac in CrFK cells infected with FHV-Cap/Lac as recombinant FHV-1 was analyzed by the following immunofluorescence assay.

That is, FHV-Cap/Lac was added in a MOI of 0.01 to $1\times10^6$ CrFK cells, and the cells were infected with the virus through adsorption in the same manner as described above, and then the cells were cultured at 37° C. for 24 hours in D-MEM medium containing 2% fetal bovine serum in the presence of 5% carbon dioxide gas. Then, the cultured cells were washed with a phosphate buffer (137 mM sodium chloride, 2.68 mM potassium chloride, 8.1 mM disodium hydrogen phosphate and 1.47 mM potassium dihydrogen phosphate, pH 7.4) and then fixed in cold acetone. The expression of FCV capsid protein and β-galactosidase in the FHV-Cap/Lac-infected CrFK cells thus fixed was analyzed in the following immunofluorescence assay.

Analysis of expression of FCV capsid protein was conducted in the following procedures. The fixed CrFK cells were reacted at 37° C. for 1 hour with mouse anti-FCV capsid protein monoclonal antibody (obtained from Dr. T. Miyazawa, Department of Agriculture, Tokyo University) diluted at 1:100with a phosphate buffer, and the cells were washed 3 times with a phosphate buffer and then reacted at 37° C. for 1 hour with tetramethylrhodamine-5-(and-6)-isothiocyanate (TRITC)-labeled goat anti-mouse IgG antibody (ICN Pharmaceuticals) diluted at 1:1,000. Then, the cells were washed 3 times with a phosphate buffer, and the expression of FCV capsid protein was observed under a fluorescence microscope. CrFK cells not infected with FHV-Cap/Lac were treated as the negative control in the same manner as described above.

Figure 8A:
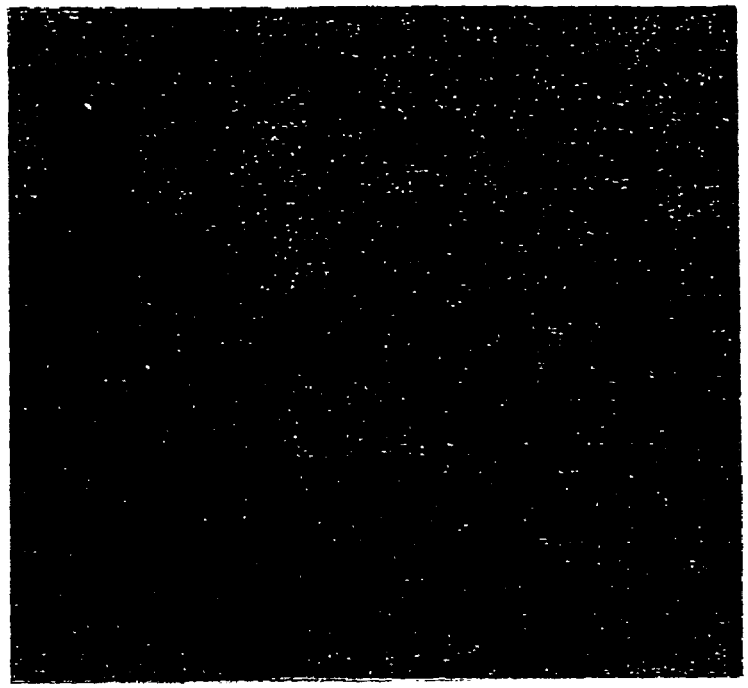
Figure 8B:
Figure 9A:
Figure 9B:
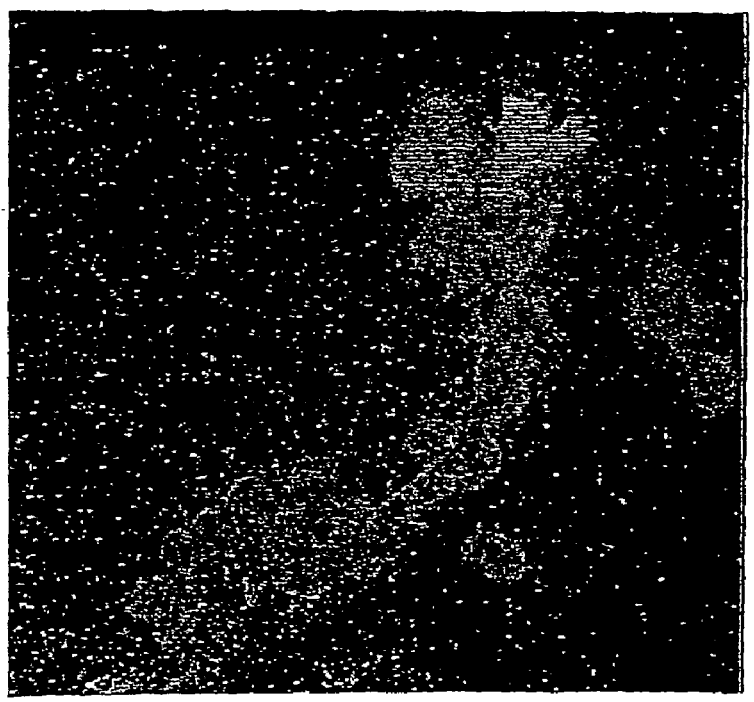

As a result of examination under a microscope, as shown in FIG. 8B, specific red fluorescence not detected in the negative control CrFK cells not infected with FHV-Cap/Lac was detected in the CrFK cells infected with FHV-Cap/Lac, thus revealing that the capsid protein of FCV from FHV-Cap/Lac is expressed and produced in the CrFK cells.

With respect to the expression of β-galactosidase from FHV-Cap/Lac, rabbit anti-β-galactosidase serum (Chemicon International) diluted at 1:100 as primary antibody and fluorescein isothiocyanate (FITC)-labeled goat anti-rabbit IgG serum (Wako Pure Chemical Industries, Ltd.) diluted at 1:2,000 as secondary antibody were added to and reacted with the CrFK cells infected with FHV-Cap/Lac prepared in the same manner as described above, and the fluorescence-labeled β-galactosidase was detected by observation under a fluorescence microscope. CrFK cells not infected with FHV-Cap/Lac were also used as the negative control in this experiment.

As shown in the results in FIG. 8A, green fluorescence-labeled β-galactosidase was detected in the CrFK cells infected with FHV-Cap/Lac, but not in the negative control CrFK cells not infected with FHC-Cap/Lac, thus revealing that β-galactosidase from FHV-Cap/Lac is expressed and produced in the CrFK cells.

In a double staining method wherein the indirect immunofluorescence assay for detection of FCV capsid protein and the immunofluorescence assay for detection of β-galactosidase were simultaneously conducted, red fluorescence-labeled FCV capsid protein and green fluorescence-labeled β-galactosidase were detected on the same cell, thus revealing that both FCV capsid protein and β-galactosidase are simultaneously expressed and produced in the CrFK cells infected with FHV-Cap/Lac.

From these results, it was proved that FHV-Cap/Lac as recombinant FHV-1 can be replicated in established feline cell lines and can simultaneously express capsid protein and β-galactosidase respectively from the FCV capsid protein gene and LacZ gene inserted as foreign genes.

EXAMPLE 6

Production of Antibodies in Cats (1) Preparation of FHV-Cap/Lac $1\times10^7$ CrFK cells were infected by adsorption with FHV-Cap/Lac in MOI of 0.01 in the same manner as described above. Then, the infected CrFK cells were cultured at 37° C. in the presence of 5% carbon dioxide gas in D-MEM medium containing 2% fetal bovine serum for about 4 days until CPE was recognized in almost all cells. Then, the cultured cell suspension was frozen and thawed 3 times to disrupt the cells, and FHV-Cap/Lac was obtained in a centrifuged supernatant of the disrupted cell solution.

(2) Detection of Anti-β Galactosidase Antibody, Anti-FHV-1 Antibody and Anti-Capsid Antibody in Cats Inoculated with FHV-Cap/Lac 2 ml of $2\times10^6$ $TCID_{50}$/ml FHV-Cap/Lac was inoculated nasally, orally and via the eyes into three one-year-old male cats respectively, and 3 weeks thereafter, each cat was given a booster under the same conditions. Five days after this booster, blood was collected from the cervical artery of each cat, and the anti-β-galactosidase antibody in serum prepared from the blood was detected by the indirect immunofluorescence assay, while the anti-FHV-1 antibody was detected by a neutralization test with FHV-1, and the anti-capsid antibody was detected by the indirect immunofluorescence assay. Hereinafter, the indirect immunofluorescence assay, the neutralization test method and the results are described.

(2-1) Detection of the Anti-β-Galactosidase Antibody 0.3 μg of β-galactosidase expression plasmid vector pCMVβ was reacted with 2 μl of a commercial transfection reagent LipofectAMINE (GIBCO BRL) at room temperature for 45 minutes, and the reaction product was added to $8\times10^4$ CrFK cells cultured on an 8-wells culture slide glass (BECTON DIKINSON), to introduce the pCMVβ DNA into the cells. Then, the CrFK cells into which the gene had been introduced were cultured at 37° C. in the presence of 5% carbon dioxide gas for 24 hours and then washed 3 times with a phosphate buffer, before being fixed in cold acetone.

Separately, prior to the indirect immunofluorescence assay, the serum from the cat inoculated with FHV-Cap/Lac was mixed with a centrifuged supernatant of the disrupted CrFK cell solution, in the same amount as the serum, and by an adsorption procedure at 37° C. for 30 minutes, nonspecific antigen-antibody reaction was reduced. This feline serum was diluted at 1:20 with a phosphate buffer and used as primary antibody.

The acetone-fixed CrFK cells prepared above were reacted at 37° C. for 1 hour with 100 μl of the feline serum diluted at 1:20, and then washed 3 times with a phosphate buffer and then reacted at 37° C. for 1 hour with FITC-labeled goat anti-cat IgG antibody (ICN/CAPPEL) diluted at 1:1,000 with a phosphate buffer. Then, the cells were washed 3 times with a phosphate buffer and fluorescence-labeled β-galactosidase in the CrFK cells was detected by a fluorescence microscope. CrFK cells not transfected with pCMVβ, and the serum of the cat before inoculation with FHV-Cap/Lac, were examined respectively as the negative control by the indirect immunofluorescence assay in the same manner as described above.

As shown in FIG. 9, fluorescence-labeled β-galactosidase was not detected in the case where, as the negative control, the CrFK cells into which pCMVβ DNA had not been introduced, and the serum of the cat, before inoculation with FHV-Cap/Lac, were used (FIG. 9A), but was detected in pcMVβ DNA-containing CrFK cells reacted with the serum of the cat inoculated with FHV-Cap/Lac (FIG. 9B). This result revealed that the FHV-Cap/Lac inoculated into the cat body is replicated, and β-galactosidase is produced from the FHV-Cap/Lac.

(2-2) Measurement of the Anti-FHV-1 Antibody

100 μl serum of the cat inoculated with FHV-Cap/Lac diluted stepwise twice with D-MEM medium and 100 μl FHV-1 liquid prepared at $6\times10^2$ $TCID_{50}$/ml were incubated for 1 hour in a 96-wells tissue culture plate at 37° C. in the presence of 5% carbon dioxide gas, then 100 μl of the incubated sample was added to $2\times10^5$ CrFK cells in a 24-wells for tissue culture plate and incubated for 1 hour at 37° C. in the presence of 5% carbon dioxide gas, to infect the CrFK cells by adsorption with FHV-1.

Then, the cell culture solution was removed, and 300 μl D-MEM soft agar medium containing 2% fetal bovine serum and 1% agarose was layered on the CrFC cells and incubated for 2 days, then 300 μl D-MEM soft agar medium containing 0.01% neutral red, 1% fetal bovine serum and 1% agarose was layered on the cells, and the number of plaques of viruses proliferated incubated for 24 hours was counted. The degrees of dilution of the feline serum at which the number of these plaques was half or less of the number of plaques appearing in CrFK cells infected with FHV-1 treated with serum of a cat not infected with FHV-Cap/Lac were determined, and the reciprocal of the highest degree of dilution of the feline serum was regarded as the neutralizing antibody titer. In the measurement of the neutralizing antibody titer, serum from the three cats inoculated with FHV-Cap/Lac showed 8-, 16- and 16-fold neutralizing antibody titer, respectively. As a result, it was confirmed that the FHV-Cap/Lac inoculated into the cats is replicated.

(2-3) Measurement of the Anti-Calicivirus Capsid Protein Antibody

100 µl of $8\times10^3$ TCID$_{50}$/ml feline calicivirus F4 strain viral liquid was added to $8\times10^4$ CrFK cells cultured on a 8-wells culture slide glass (BECTON DIKINSON), and incubated at 37° C. in the presence of 5% carbon dioxide gas for 1 hour, to infect the CrFK cells through adsorption with the feline calicivirus F4 strain. Then, the cells were washed with D-MEM medium and then cultured at 37° C. in the presence of 5% carbon dioxide gas for 2 days in D-MEM medium containing 2% fetal bovine serum. The cultured cells infected with the feline calicivirus F4 strain were washed 3 times with a phosphate buffer and then fixed in cold acetone.

Separately, prior to the indirect immunofluorescence assay, the serum from the cat inoculated with FHV-Cap/Lac was mixed with an equal volume of a centrifuged supernatant of the disrupted CrFK cell solution, and by an adsorption procedure at 37° C. for 30 minutes, nonspecific antigen-antibody reaction was reduced. Then, this feline serum was diluted at 1:8 with a phosphate buffer and used as primary antibody.

The acetone-fixed CrFK cells infected with the feline calicivirus, prepared in the manner described above, were reacted at 37° C. for 1 hour with 100 µl serum, diluted at 1:8, of the cat infected with FHV-Cap/Lac, and then the cells were washed 3 times with a phosphate buffer and reacted at 37° C. for 1 hour with FITC-labeled goat anti-cat IgG antibody (ICN/CAPPEL) diluted at 1:1,000 with a phosphate buffer. Then, the cells were washed 3 times with a phosphate buffer and fluorescence-labeled feline calicivirus capsid protein was detected in the CrFK cells by a fluorescence microscope. CrFK cells not infected with feline calicivirus and the serum of a cat before inoculation with FHV-Cap/Lac were examined respectively as the negative control by the indirect immunofluorescence assay in the same manner as described above. The results are shown in FIG. 10.

Figure 10A:
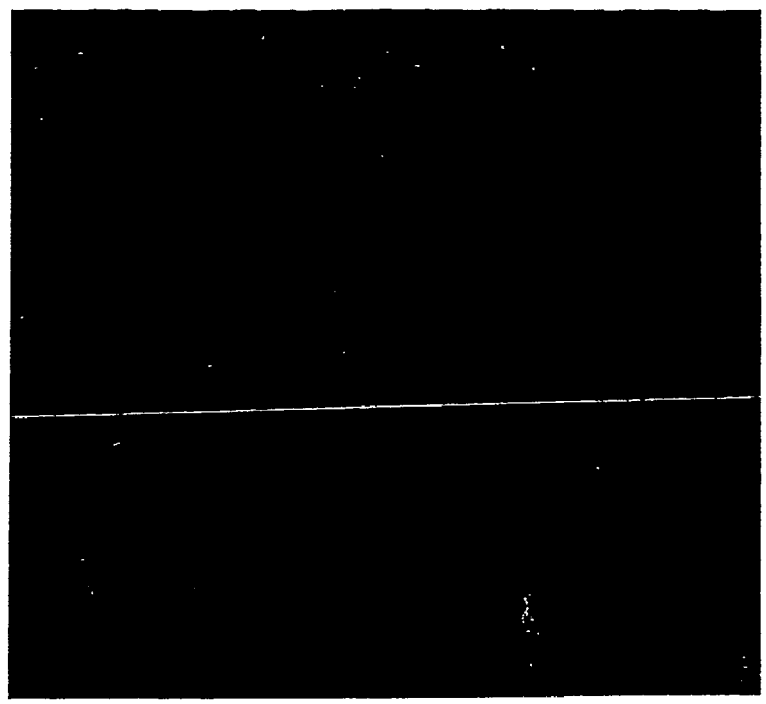
Figure 10B:

As shown in FIG. 10A, fluorescence-labeled feline calicivirus capsid protein was not detected in the case where as the negative control, the serum of the cat before inoculation with FHV-Cap/Lac was reacted with the CrFK cells infected with the feline calicivirus. Further, fluorescence-labeled feline calicivirus capsid protein was not detected in the case where the serum of the cat inoculated with FHV-Cap/Lac was reacted with CrFK cells not infected with the feline calicivirus (not shown in the figure). That is, the fluorescence-labeled feline calicivirus capsid protein was detected in only the case where the serum of the cat inoculated with FHV-Cap/Lac was reacted with the CrFK cells infected with the feline calicivirus, as shown in FIG. 10B. This result revealed that the inoculated FHV-Cap/Lac is replicated in the cat body, and the feline calicivirus F4 strain capsid protein is produced from the FHV-Cap/Lac.

From these results, it is found that when FHV-Cap/Lac is inoculated via the mucosa into a cat, the inoculated cat while maintaining healthy conditions produces three types of antibodies, that is, an antibody to FHV-1, an antibody to a feline calicivirus capsid protein as a product of the foreign gene inserted into the thymidine kinase region and an antibody to β-galactosidase as a product of the foreign gene inserted into the BamHI site in the I fragment. Thus the insertion sites for the foreign genes in the recombinant FHV-1 in this invention do not affect replication of the virus itself, and the foreign genes integrated in these insertion sites produce proteins respectively.

That is, this recombinant virus can be inoculated into a cat via the mucosa i.e. orally or via the nose or eyes to endow the cat with immunity not only to FHV-1 but also to products of at least two foreign genes, and by inoculating this recombinant virus vector FHV-Cap/Lac orally or via the nose or eyes into a cat, the inoculated cat, while maintaining healthy conditions, actually produces antibodies to the calicivirus capsid protein, β-galactosidase and virus vector FHV-1.

7. Determination of a Partial Nucleotide Sequence of the SalI I Fragment in the Feline Herpesvirus Type 1 Genome (1) Determination of the Sequence A partial nucleotide sequence of the FHV-1 genome-derived SalI I fragment integrated in plasmid pdBSI (see FIG. 1) was determined using a DNA sequencer (Pharmacia). Hereinafter, this is described in more detail.

A 1969-bp partial DNA fragment (PstI-HindIII DNA fragment) was cleaved from the SalI I fragment of FHV-1 integrated in pdBSI, and then integrated in a PstI-Hind-III digested site of a commercial cloning vector pBluescript II SK(+) (Stratagene). The resulting plasmid harboring a partial nucleotide sequence of the SalI I fragment of FHV-1 was designated pSal-Hind. Then, about 600-bp nucleotide sequences from the 5'- and 3'-ends of the PstI-HindIII DNA fragment were determined respectively by a cycle sequence method by using the pSal-Hind plasmid DNA as the template, a forward primer (M13 Universal primer, 5'-CGACGTTGTAAAACGACGGCCAGT, SEQ ID NO:3) and a reverse primer (M13 Reverse primer, 5'-CAGGAAACAGCTATGAC, SEQ ID NO:4) located upward and downward respectively from the PstI-HindIII DNA fragment. Further, four types of new primers (Primer X1, SEQ ID NO:5; Primer X2, SEQ ID NO:6; Primer X3, SEQ ID NO:7; and Primer X4, SEQ ID NO:8) were synthesized on the basis of the determined nucleotide sequences at the 5'- and 3'-ends of the PstI-HindIII DNA fragment, and the whole nucleotide sequence, 1969 nucleotides, of the PstI-HindIII DNA fragment was determined by a primer-walking method. The determined nucleotide sequence of the Pst-HindIII DNA fragment in the SalI I fragment derived from the FHV-1 genome is set forth in SEQ ID NO:1. An amino acid sequence deduced from the nucleotide sequence shown in SEQ ID NO:1 is set forth in SEQ ID NO:2.

(2) Comparative Analysis of the Amino Acid Sequence Encoded by the Nucleotide Sequence of the SalI I Fragment in the Feline Herpesvirus Type 1 Genome The amino acid sequence deduced from the nucleotide sequence (PstI-HindIII DNA fragment) in the vicinity of the BamHI-digested site in the SalI I fragment present in the $U_L$ region of the FHV-1 genome, which is set forth in SEQ ID NO:2, was compared with an amino acid sequence of protein kinase present in the $U_L$ region of each of herpes simplex virus type 1 (HSV-1), equine herpesvirus type 1 (EHV-1) and equine herpesvirus type 4 (EHV-4) (R. F. Smith, and T. F. Smith, 1989, J. Virol. 63: 450-455, GenBank accession number: EHV-1, NC001491; EHV-4, NC001844) as shown in FIG. 11. As is evident from comparison among the respective amino acid sequences shown in FIG. 11, the amino acid sequences of the catalytic domains I to VI in protein kinase, enclosed with the square, were conserved highly among herpesviruses such as FHV-1, HSV-1, EHV-1 and EHV-4. In particular, with respect to the amino acid sequence encoded by the PstI-HindIII DNA fragment in the SalI I fragment of FHV-1, the amino acids corresponding to the constituent amino acids of each catalytic domain in protein kinase recognized therein are different in some cases from the constituent amino acids of each catalytic domain in protein kinase in HSV-1, but are identical in many cases with the constituent amino acids of each catalytic domain in protein kinase in EH1 and EH-4.

From the analysis described above, the nucleotide sequence in the vicinity of the BamHI-digested site in the $U_L$ region SalI I fragment as the foreign gene insertion site found in this invention was revealed to encode protein kinase.

On one hand, the finding that protein kinase in the $U_L$ region of a psuedorabies virus belonging to the same alpha-herpesvirus subfamily as that of FHV-1 is not essential for proliferation and replication of the virus has been reported (N. deWind, J. Domen, and A. Berns, 1992, J. Virol. 66: 5200-5209).

Taking these analysis results of the amino acid sequences and the finding that the protein kinase in the $U_L$ region in the herpesvirus is not essential for replication and proliferation of the virus into consideration, it could be seen that the gene in the vicinity of the BamHI in the I fragment is a part of the gene encoding protein kinase in the $U_L$ region, and that the gene product protein kinase is not essential for replication and proliferation of the virus. Furthermore, it was revealed that the foreign gene insertion sites found in this invention are not limited to the BamHI-digested site in the SalI I fragment in the FHV-1 genome, and may be in the region of the protein kinase gene in the $U_L$ region in the FHV-1 genome.

INDUSTRIAL APPLICABILITY

According to this invention, a recombinant FHV-1 vector capable of expressing and producing products of at least two types of foreign genes can be prepared, and this recombinant FHV-1 vector can be used as a safe and polyvalent vaccine virus.

The invention claimed is:

1. An attenuated recombinant feline herpesvirus type 1 comprising at least two types of foreign genes inserted in such a manner as to allow the expression thereof into two different regions in the recombinant feline herpesvirus type 1 genome, wherein one of the two different regions is the I fragment region present in the unique long ($U_L$) region out of the SalI cleaved-DNA fragments of the feline herpesvirus type 1 genome and one of the two different regions is a gene region encoding thymidine kinase.

2. The attenuated recombinant feline herpesvirus type 1 according to claim 1, wherein the two different regions in the feline herpesvirus type 1 genome exert no lethal effect on the proliferation of the feline herpesvirus type 1.

3. The attenuated recombinant feline herpesvirus type 1 according to claim 1, wherein the two different regions in the feline herpesvirus type 1 genome are two gene regions i.e. a gene region encoding protein kinase in the unique long ($U_L$) region of the feline herpesvirus type 1 genome and a gene region encoding thymidine kinase.

4. The attenuated recombinant feline herpesvirus type 1 according to claim 2, wherein the two regions exerting no lethal effect on the proliferation of the feline herpesvirus type 1 are two gene regions i.e. a gene region encoding protein kinase in the unique long ($U_L$) region of the feline herpesvirus type 1 genome and a gene region encoding thymidine kinase.

5. The attenuated recombinant feline herpesvirus type 1 according to claim 1, wherein one of the two different regions is the I fragment region present in a gene region encoding protein kinase.

6. The attenuated recombinant feline herpesvirus type 1 according to claim 5, wherein one of the two different regions is a BamHI cleaved site of the I fragment region.

7. An attenuated recombinant feline herpesvirus type 1 comprising two types of foreign genes inserted in such a manner as to allow the expression thereof into two different regions in the recombinant feline herpesvirus type 1 genome, wherein one of the two different regions is the I fragment region present in the unique long ($U_L$) region out of the SalI cleaved-DNA fragments of the feline herpesvirus type 1 genome.

8. A method of introducing foreign genes, which comprises infecting cells with the attenuated recombinant feline herpesvirus type 1 described in claim 1.

9. An immunizing method which comprises inoculating the attenuated recombinant herpesvirus type 1 described in claim 1 into an animal via the mucosa or by injection to give immunity to the inoculated animal.

* * * * *

SEQUENCE LISTING

```
<160> NUMBER OF SEQ ID NOS: 8

<210> SEQ ID NO 1
<211> LENGTH: 1969
<212> TYPE: DNA
<213> ORGANISM: Feline Herpesvirus Type 1
<220> FEATURE:
<221> NAME/KEY: CDS
<222> LOCATION: (361)..(1968)
<223> OTHER INFORMATION:

<400> SEQUENCE: 1
agcttaccaa cgtgaatcaa tatttaaggc acgtacgcta gacatgatcc gtggagggat      60
agataggcgt gatcctattt ttgttcacac atttacgtca gcaaaacggg ccgggcaggc     120
cttgacagac aactacacac atactctagg gtggaggcga tagaacaaaa gacacaatca     180
ctgcgactgc gcattgaggc acagacgccg tcgaagaagt actgcatagc catcgacggt     240
atctccagtc agacttcact gataaaattg atgctgtgga tgataagata tttgaaaagg     300
aaaatcaatt aaccgaaact attctagaag tagatccaga cccgaaactc tggaacgtgg     360 atg gct aga cga ggc gga cga agc gct act gac gag atg gat gtt ggc       408
Met Ala Arg Arg Gly Gly Arg Ser Ala Thr Asp Glu Met Asp Val Gly
1               5                   10                  15 gga agc tcc caa ggc gac cca ctg tca cat gga cca ata ctc tca cct       456
Gly Ser Ser Gln Gly Asp Pro Leu Ser His Gly Pro Ile Leu Ser Pro
            20                  25                  30 atc aca aga cca tca tcg ggg gtc cgg gaa ggg ggg gga cat tgc aac       504
Ile Thr Arg Pro Ser Ser Gly Val Arg Glu Gly Gly Gly His Cys Asn
        35                  40                  45 acg gcc gat ccc cac tct caa gga aac cat atc aaa cgg ggt ata tgt       552
Thr Ala Asp Pro His Ser Gln Gly Asn His Ile Lys Arg Gly Ile Cys
    50                  55                  60 aaa cca gga gtc tct gga tcc ggt aac aca gcc gat agc gct cac aaa       600
Lys Pro Gly Val Ser Gly Ser Gly Asn Thr Ala Asp Ser Ala His Lys
65                  70                  75                  80 cac ctc acc atg tcc cca agg agg ctg cgc cca tta cca cac aga gaa       648
His Leu Thr Met Ser Pro Arg Arg Leu Arg Pro Leu Pro His Arg Glu
                85                  90                  95
```

```
ggg atc tta cgt cac cgg att aaa gaa gaa tgt caa gac ttt cag gct      696
Gly Ile Leu Arg His Arg Ile Lys Glu Glu Cys Gln Asp Phe Gln Ala
            100                 105                 110 ggt aac gga gaa ggt aaa atc agg gca aac acc gcc atc gac aga tat      744
Gly Asn Gly Glu Gly Lys Ile Arg Ala Asn Thr Ala Ile Asp Arg Tyr
        115                 120                 125 ttt aca cga gcg aga cgt atc ttc aaa tat aca ccc aga cgc atg tct      792
Phe Thr Arg Ala Arg Arg Ile Phe Lys Tyr Thr Pro Arg Arg Met Ser
130                 135                 140 agt aga cga ggc ggg aga acc act ccc cca tgt atg gct ggg tgg gct      840
Ser Arg Arg Gly Gly Arg Thr Thr Pro Pro Cys Met Ala Gly Trp Ala
145                 150                 155                 160 tcc ccc tct ggt gga cga tat gac ggg ctc att cga ggg gac tcc aac      888
Ser Pro Ser Gly Gly Arg Tyr Asp Gly Leu Ile Arg Gly Asp Ser Asn
                165                 170                 175 aat gga cgg acc gat ata cca aat acc ctg act cga att cct ata cat      936
Asn Gly Arg Thr Asp Ile Pro Asn Thr Leu Thr Arg Ile Pro Ile His
            180                 185                 190 gag gta tgt acc cca tta aca aca aat ccc ggc aac agg tca tct att      984
Glu Val Cys Thr Pro Leu Thr Thr Asn Pro Gly Asn Arg Ser Ser Ile
        195                 200                 205 ttg aaa att agg aaa att aag cgt gtt acg atc cct gtg ttc tca gtg     1032
Leu Lys Ile Arg Lys Ile Lys Arg Val Thr Ile Pro Val Phe Ser Val
210                 215                 220 tca gca gaa atg cat tac tct aag gtg gca cta gga gaa cca ccg aag     1080
Ser Ala Glu Met His Tyr Ser Lys Val Ala Leu Gly Glu Pro Pro Lys
225                 230                 235                 240 ttc ggg ggg gct ggt ggg tat gga gaa gta cag att tat cga caa aca     1128
Phe Gly Gly Ala Gly Gly Tyr Gly Glu Val Gln Ile Tyr Arg Gln Thr
                245                 250                 255 ggt ctg gcc atc aaa aca tca tca agt cca tcg tgt ttt gaa cat gaa     1176
Gly Leu Ala Ile Lys Thr Ser Ser Ser Pro Ser Cys Phe Glu His Glu
            260                 265                 270 tta tta gtc act tta tta gcc ggg gag agc tct cta cgc gct aga tca     1224
Leu Leu Val Thr Leu Leu Ala Gly Glu Ser Ser Leu Arg Ala Arg Ser
        275                 280                 285 tcc ata ggc ata act ggg ata att tac ccc gtt gca ttt tca tta acc     1272
Ser Ile Gly Ile Thr Gly Ile Ile Tyr Pro Val Ala Phe Ser Leu Thr
290                 295                 300 gaa cac caa atg gta ttc aaa gcg tat gat atg gat ctg aat gta tat     1320
Glu His Gln Met Val Phe Lys Ala Tyr Asp Met Asp Leu Asn Val Tyr
305                 310                 315                 320 tgt aat aaa cta tca tcc gct gga ccc cca aca tca aat ata ctt aat     1368
Cys Asn Lys Leu Ser Ser Ala Gly Pro Pro Thr Ser Asn Ile Leu Asn
                325                 330                 335 gcg atg gaa cat gcg ttc atc ggg ttg ggt aag gct gtg gca tac ctg     1416
Ala Met Glu His Ala Phe Ile Gly Leu Gly Lys Ala Val Ala Tyr Leu
            340                 345                 350 aac acc aaa tgc ggc tta acg cat ttg gat atc aaa tgt gga aat ata     1464
Asn Thr Lys Cys Gly Leu Thr His Leu Asp Ile Lys Cys Gly Asn Ile
        355                 360                 365 ttc gtc aac aca aaa aat tgt gtt ata aaa gat tat gtc ata gcc gat     1512
Phe Val Asn Thr Lys Asn Cys Val Ile Lys Asp Tyr Val Ile Ala Asp
370                 375                 380 ttt agt ctg atg act cta aac aca aat tct acc gta atg cgg gcg gag     1560
Phe Ser Leu Met Thr Leu Asn Thr Asn Ser Thr Val Met Arg Ala Glu
385                 390                 395                 400 ttt gaa att ccc act ggg gat gcg tca aat aag gtc cta cgc ctt tca     1608
Phe Glu Ile Pro Thr Gly Asp Ala Ser Asn Lys Val Leu Arg Leu Ser
                405                 410                 415
```

-continued

```
cga ggg gcg gcg aca act ata ttt agt ctg gta ttg ggt cat gga cat        1656
Arg Gly Ala Ala Thr Thr Ile Phe Ser Leu Val Leu Gly His Gly His
        420                 425                 430 aac caa ccc acg gag ata ctg gtt gac ttt att aat aac agt gga ctg        1704
Asn Gln Pro Thr Glu Ile Leu Val Asp Phe Ile Asn Asn Ser Gly Leu
            435                 440                 445 gct cga cac cgc ggc cca tta gac agt gac gtt ggt gta gct gtt gac        1752
Ala Arg His Arg Gly Pro Leu Asp Ser Asp Val Gly Val Ala Val Asp
450                 455                 460 ttg tat gct ctt gga cag gtg cta ttg gaa ctg ctt ttg act gga tgc        1800
Leu Tyr Ala Leu Gly Gln Val Leu Leu Glu Leu Leu Leu Thr Gly Cys
465                 470                 475                 480 ctt tcc cct cgg tta ccg gtc ccc att ctt aga aat acg aca tat tac        1848
Leu Ser Pro Arg Leu Pro Val Pro Ile Leu Arg Asn Thr Thr Tyr Tyr
                485                 490                 495 tac tac cta cac cag gtg acc gtg gaa tat gcc ttg gat ctc tta gca        1896
Tyr Tyr Leu His Gln Val Thr Val Glu Tyr Ala Leu Asp Leu Leu Ala
            500                 505                 510 tat ctg cgc act ata ccc cca tat att tcc ttc ttc acc tat tac aac        1944
Tyr Leu Arg Thr Ile Pro Pro Tyr Ile Ser Phe Phe Thr Tyr Tyr Asn
        515                 520                 525 aat tca tgg tgt tcc ata ccc tgc a                                      1969
Asn Ser Trp Cys Ser Ile Pro Cys
    530                 535

<210> SEQ ID NO 2
<211> LENGTH: 536
<212> TYPE: PRT
<213> ORGANISM: Feline Herpesvirus Type 1

<400> SEQUENCE: 2

Met Ala Arg Arg Gly Gly Arg Ser Ala Thr Asp Glu Met Asp Val Gly
1               5                   10                  15

Gly Ser Ser Gln Gly Asp Pro Leu Ser His Gly Pro Ile Leu Ser Pro
            20                  25                  30

Ile Thr Arg Pro Ser Ser Gly Val Arg Glu Gly Gly His Cys Asn
        35                  40                  45

Thr Ala Asp Pro His Ser Gln Gly Asn His Ile Lys Arg Gly Ile Cys
    50                  55                  60

Lys Pro Gly Val Ser Gly Ser Gly Asn Thr Ala Asp Ser Ala His Lys
65                  70                  75                  80

His Leu Thr Met Ser Pro Arg Arg Leu Arg Pro Leu Pro His Arg Glu
                85                  90                  95

Gly Ile Leu Arg His Arg Ile Lys Glu Glu Cys Gln Asp Phe Gln Ala
            100                 105                 110

Gly Asn Gly Glu Gly Lys Ile Arg Ala Asn Thr Ala Ile Asp Arg Tyr
        115                 120                 125

Phe Thr Arg Ala Arg Arg Ile Phe Lys Tyr Thr Pro Arg Arg Met Ser
    130                 135                 140

Ser Arg Arg Gly Gly Arg Thr Thr Pro Pro Cys Met Ala Gly Trp Ala
145                 150                 155                 160

Ser Pro Ser Gly Gly Arg Tyr Asp Gly Leu Ile Arg Gly Asp Ser Asn
                165                 170                 175

Asn Gly Arg Thr Asp Ile Pro Asn Thr Leu Thr Arg Ile Pro Ile His
            180                 185                 190

Glu Val Cys Thr Pro Leu Thr Thr Asn Pro Gly Asn Arg Ser Ser Ile
        195                 200                 205
```

-continued

```
Leu Lys Ile Arg Lys Ile Lys Arg Val Thr Ile Pro Val Phe Ser Val
    210                 215                 220
Ser Ala Glu Met His Tyr Ser Lys Val Ala Leu Gly Glu Pro Pro Lys
225                 230                 235                 240
Phe Gly Gly Ala Gly Gly Tyr Gly Glu Val Gln Ile Tyr Arg Gln Thr
                245                 250                 255
Gly Leu Ala Ile Lys Thr Ser Ser Pro Ser Cys Phe Glu His Glu
            260                 265                 270
Leu Leu Val Thr Leu Leu Ala Gly Glu Ser Ser Leu Arg Ala Arg Ser
                275                 280                 285
Ser Ile Gly Ile Thr Gly Ile Ile Tyr Pro Val Ala Phe Ser Leu Thr
            290                 295                 300
Glu His Gln Met Val Phe Lys Ala Tyr Asp Met Asp Leu Asn Val Tyr
305                 310                 315                 320
Cys Asn Lys Leu Ser Ser Ala Gly Pro Pro Thr Ser Asn Ile Leu Asn
                325                 330                 335
Ala Met Glu His Ala Phe Ile Gly Leu Gly Lys Ala Val Ala Tyr Leu
            340                 345                 350
Asn Thr Lys Cys Gly Leu Thr His Leu Asp Ile Lys Cys Gly Asn Ile
        355                 360                 365
Phe Val Asn Thr Lys Asn Cys Val Ile Lys Asp Tyr Val Ile Ala Asp
    370                 375                 380
Phe Ser Leu Met Thr Leu Asn Thr Asn Ser Thr Val Met Arg Ala Glu
385                 390                 395                 400
Phe Glu Ile Pro Thr Gly Asp Ala Ser Asn Lys Val Leu Arg Leu Ser
                405                 410                 415
Arg Gly Ala Ala Thr Thr Ile Phe Ser Leu Val Leu Gly His Gly His
            420                 425                 430
Asn Gln Pro Thr Glu Ile Leu Val Asp Phe Ile Asn Asn Ser Gly Leu
        435                 440                 445
Ala Arg His Arg Gly Pro Leu Asp Ser Asp Val Gly Val Ala Val Asp
    450                 455                 460
Leu Tyr Ala Leu Gly Gln Val Leu Leu Glu Leu Leu Thr Gly Cys
465                 470                 475                 480
Leu Ser Pro Arg Leu Pro Val Pro Ile Leu Arg Asn Thr Thr Tyr Tyr
                485                 490                 495
Tyr Tyr Leu His Gln Val Thr Val Glu Tyr Ala Leu Asp Leu Leu Ala
            500                 505                 510
Tyr Leu Arg Thr Ile Pro Pro Tyr Ile Ser Phe Phe Thr Tyr Tyr Asn
        515                 520                 525
Asn Ser Trp Cys Ser Ile Pro Cys
    530                 535

<210> SEQ ID NO 3
<211> LENGTH: 24
<212> TYPE: DNA
<213> ORGANISM: Artificial Sequence
<220> FEATURE:
<223> OTHER INFORMATION: M13 Universal primer

<400> SEQUENCE: 3
cgacgttgta aaacgacggc cagt                                        24

<210> SEQ ID NO 4
<211> LENGTH: 17
```

```
<212> TYPE: DNA
<213> ORGANISM: Artificial Sequence
<220> FEATURE:
<223> OTHER INFORMATION: M13 Reverse primer

<400> SEQUENCE: 4
caggaaacag ctatgac                                                      17

<210> SEQ ID NO 5
<211> LENGTH: 22
<212> TYPE: DNA
<213> ORGANISM: Artificial Sequence
<220> FEATURE:
<223> OTHER INFORMATION: Primer X1

<400> SEQUENCE: 5
tagtagacga ggcgggagaa cc                                                22

<210> SEQ ID NO 6
<211> LENGTH: 22
<212> TYPE: DNA
<213> ORGANISM: Artificial Sequence
<220> FEATURE:
<223> OTHER INFORMATION: Primer X2

<400> SEQUENCE: 6
aatagatgac ctgttgccgg ga                                                22

<210> SEQ ID NO 7
<211> LENGTH: 23
<212> TYPE: DNA
<213> ORGANISM: Artificial Sequence
<220> FEATURE:
<223> OTHER INFORMATION: Primer X3

<400> SEQUENCE: 7
tgcgttcatc gggttgggta agg                                               23

<210> SEQ ID NO 8
<211> LENGTH: 24
<212> TYPE: DNA
<213> ORGANISM: Artificial Sequence
<220> FEATURE:
<223> OTHER INFORMATION: Primer X4

<400> SEQUENCE: 8
accttatttg acgcatcccc agtg                                              24
```